(12) United States Patent
Narasimha-Iyer et al.

(10) Patent No.: US 11,016,186 B2
(45) Date of Patent: May 25, 2021

(54) DEFECTIVE ULTRASONIC TRANSDUCER DETECTION IN AN ULTRASONIC SENSOR

(71) Applicant: InvenSense, Inc., San Jose, CA (US)

(72) Inventors: Harihar Narasimha-Iyer, San Jose, CA (US); Hao-Yen Tang, San Jose, CA (US)

(73) Assignee: InvenSense, Inc., San Jose, CA (US)

( * ) Notice: Subject to any disclaimer, the term of this patent is extended or adjusted under 35 U.S.C. 154(b) by 380 days.

(21) Appl. No.: 16/036,767

(22) Filed: Jul. 16, 2018

(65) Prior Publication Data

US 2019/0018123 A1 Jan. 17, 2019

Related U.S. Application Data

(60) Provisional application No. 62/533,307, filed on Jul. 17, 2017.

(51) Int. Cl.
| | |
|---|---|
| *G01S 15/89* | (2006.01) |
| *G01S 7/52* | (2006.01) |
| *H04R 29/00* | (2006.01) |
| *G06K 9/00* | (2006.01) |
| *A61B 17/00* | (2006.01) |

(52) U.S. Cl.
CPC ........ *G01S 7/5205* (2013.01); *G01S 15/8925* (2013.01); *G06K 9/0002* (2013.01); *H04R 29/004* (2013.01); *A61B 2017/00725* (2013.01)

(58) Field of Classification Search
CPC . G01S 7/5205; G01S 15/8925; G06K 9/0002; H04R 29/004; A61B 2017/00725
See application file for complete search history.

(56) References Cited

U.S. PATENT DOCUMENTS

| | | | |
|---|---|---|---|
| 6,543,272 B1 * | 4/2003 | Vitek | A61N 7/02 601/2 |
| 2019/0018123 A1 * | 1/2019 | Narasimha-Iyer | H04R 29/004 |

FOREIGN PATENT DOCUMENTS

| | | | | |
|---|---|---|---|---|
| WO | 0182806 A1 | 11/2001 | | |
| WO | WO-2019018861 A3 * | 3/2019 | ........... | G06K 9/0002 |

OTHER PUBLICATIONS

ISA/EP, International Search Report and Written Opinion for International Application # PCT/US2018/051190, pp. 1-17, dated Feb. 14, 2019.

Papageorgiou, et al., "Self-Calibration of Ultrasonic Transducers in an Intelligent Data Acquisition System", International Scientific Journal of Computing, 2003, vol. 2, Issue 2 Retrieved Online: URL: https://scholar.google.com/scholar?q=self-calibration+of+ultrasonic+transducers+in+an+intelligent+data+acquisition+system&hl=en&as_sdt=0&as_vis=1&oi=scholart, 2003, 9-15.

* cited by examiner

*Primary Examiner* — Daniel Pihulic

(57) ABSTRACT

In a method for detection of defective ultrasonic transducers in an in ultrasonic sensing device, an ultrasonic signal is generated at an ultrasonic sensing device comprising a plurality of ultrasonic transducers. A reflected ultrasonic signal corresponding to the ultrasonic signal is received at at least one ultrasonic transducer of the plurality of ultrasonic transducers. It is determined whether performance the at least one ultrasonic transducer is degraded based at least in part on the reflected ultrasonic signal.

31 Claims, 19 Drawing Sheets

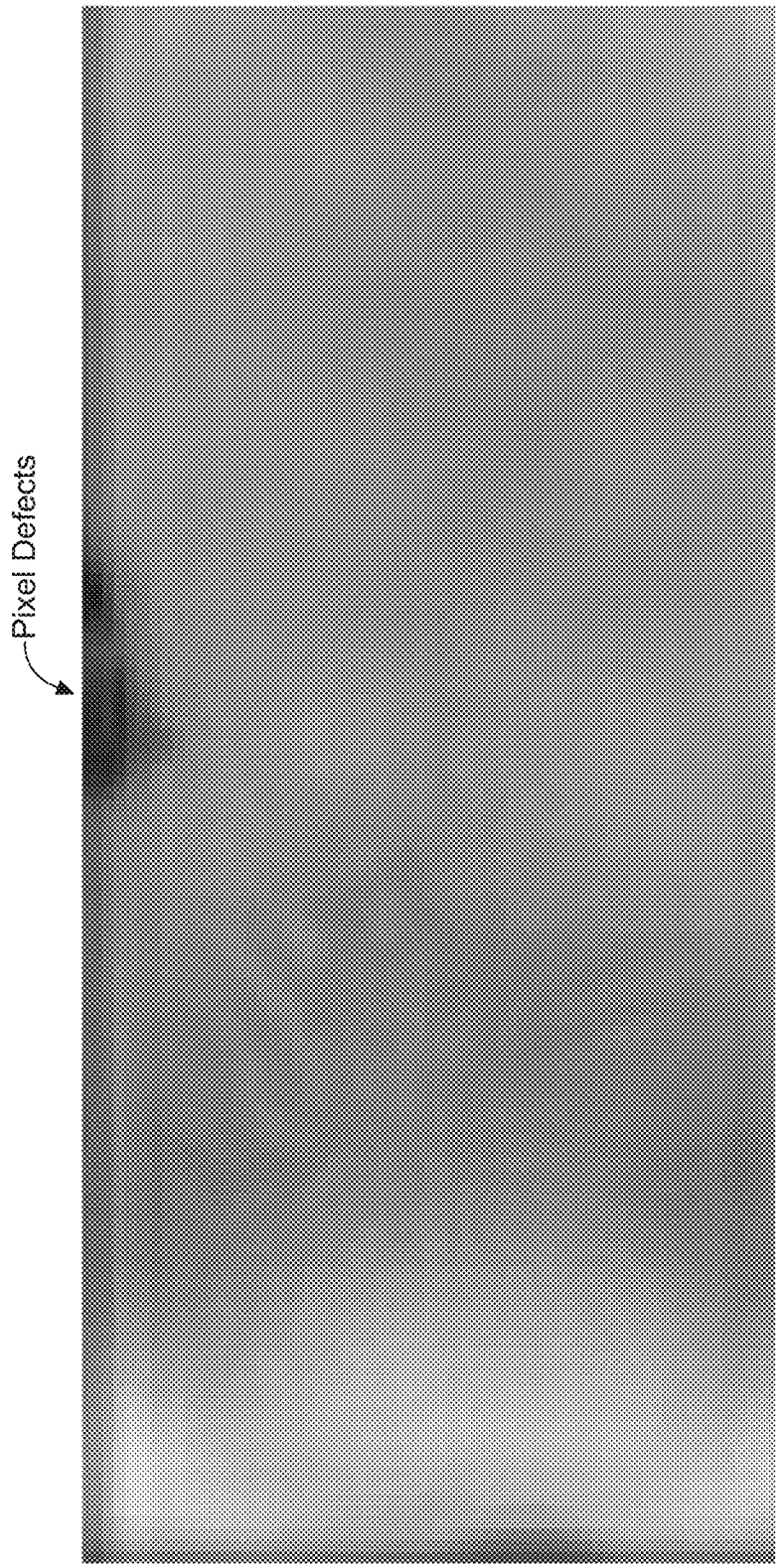

DEFECTIVE ULTRASONIC TRANSDUCER DETECTION IN AN ULTRASONIC SENSOR

RELATED APPLICATIONS

This application claims also priority to and the benefit of U.S. Provisional Patent Application 62/533,307, filed on Jul. 17, 2017, entitled "DEAD PIXEL DETECTION AND HANDLING FOR ULTRASONIC FINGERPRINT SENSORS," by Iyer, et al., and assigned to the assignee of the present application, which is incorporated herein by reference in its entirety.

BACKGROUND

Fingerprint sensors have become ubiquitous in mobile devices as well as other applications for authenticating a user's identity. They provide a fast and convenient way for the user to unlock a device, provide authentication for payments, etc. Current fingerprint sensors are typically area sensors that obtain a two-dimensional image of the user's finger area presented to the sensor. Different technologies can be used to image the finger such as capacitive, ultrasound, and optical sensing. Once an image is obtained, that image is processed by a matcher to extract features and to compare against stored images to authenticate the user. As such, accuracy of captured images is essential to the performance of image matching for user authentication.

BRIEF DESCRIPTION OF THE DRAWINGS

The accompanying drawings, which are incorporated in and form a part of the Description of Embodiments, illustrate various embodiments of the subject matter and, together with the Description of Embodiments, serve to explain principles of the subject matter discussed below. Unless specifically noted, the drawings referred to in this Brief Description of Drawings should be understood as not being drawn to scale. Herein, like items are labeled with like item numbers.

FIG. 7A illustrates an example phase delay pattern for a 9×9 ultrasonic transducer block, according to some embodiments.

FIG. 7B illustrates another example phase delay pattern for a 9×9 ultrasonic transducer block, according to some embodiments.

FIG. 12C illustrates an example image with no finger present, showing defective pixels corresponding to defective ultrasonic transducers, according to an embodiment.

DESCRIPTION OF EMBODIMENTS

Figure 1A:
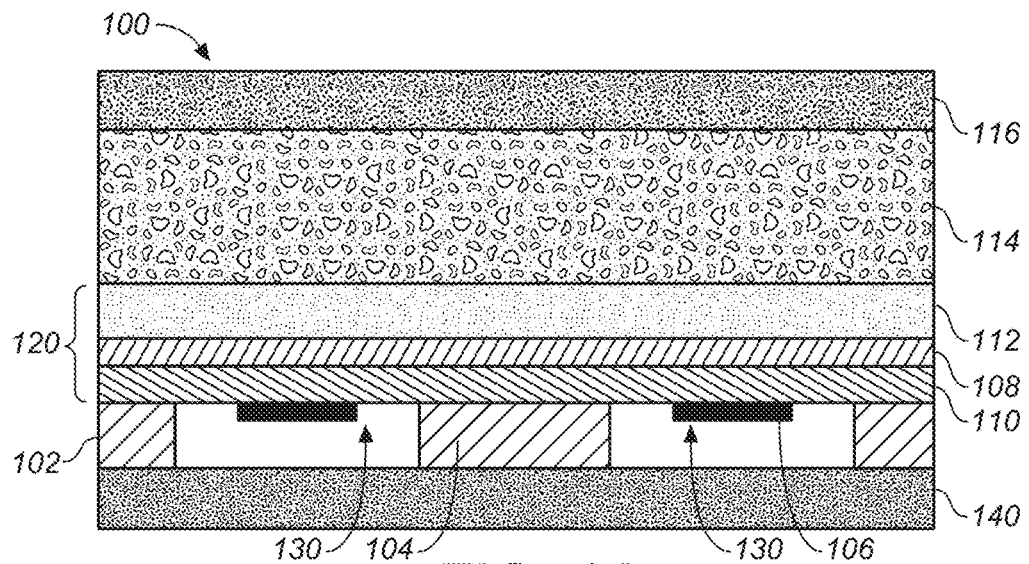
FIG. 1A is a diagram illustrating a piezoelectric micromachined ultrasonic transducer (PMUT) device having a center pinned membrane, according to some embodiments.

The following Description of Embodiments is merely provided by way of example and not of limitation. Furthermore, there is no intention to be bound by any expressed or implied theory presented in the preceding background or in the following Description of Embodiments.

Reference will now be made in detail to various embodiments of the subject matter, examples of which are illustrated in the accompanying drawings. While various embodiments are discussed herein, it will be understood that they are not intended to limit to these embodiments. On the contrary, the presented embodiments are intended to cover alternatives, modifications and equivalents, which may be included within the spirit and scope the various embodiments as defined by the appended claims. Furthermore, in this Description of Embodiments, numerous specific details are set forth in order to provide a thorough understanding of embodiments of the present subject matter. However, embodiments may be practiced without these specific details. In other instances, well known methods, procedures, components, and circuits have not been described in detail as not to unnecessarily obscure aspects of the described embodiments.

Notation and Nomenclature

Some portions of the detailed descriptions which follow are presented in terms of procedures, logic blocks, processing and other symbolic representations of operations on data within an electrical device. These descriptions and representations are the means used by those skilled in the data processing arts to most effectively convey the substance of their work to others skilled in the art. In the present application, a procedure, logic block, process, or the like, is conceived to be one or more self-consistent procedures or instructions leading to a desired result. The procedures are those requiring physical manipulations of physical quantities. Usually, although not necessarily, these quantities take the form of acoustic (e.g., ultrasonic) signals capable of being transmitted and received by an electronic device and/or electrical or magnetic signals capable of being stored, transferred, combined, compared, and otherwise manipulated in an electrical device.

It should be borne in mind, however, that all of these and similar terms are to be associated with the appropriate physical quantities and are merely convenient labels applied to these quantities. Unless specifically stated otherwise as apparent from the following discussions, it is appreciated that throughout the description of embodiments, discussions utilizing terms such as "generating," "receiving," "determining," "classifying," "comparing," "initiating," "detecting," "maintaining," "selecting," "identifying," "increasing," "providing," "adjusting," "correcting," "interpolating," or the like, refer to the actions and processes of an electronic device such as an electrical device.

Embodiments described herein may be discussed in the general context of processor-executable instructions residing on some form of non-transitory processor-readable medium, such as program modules, executed by one or more computers or other devices. Generally, program modules include routines, programs, objects, components, data structures, etc., that perform particular tasks or implement particular abstract data types. The functionality of the program modules may be combined or distributed as desired in various embodiments.

In the figures, a single block may be described as performing a function or functions; however, in actual practice, the function or functions performed by that block may be performed in a single component or across multiple components, and/or may be performed using hardware, using software, or using a combination of hardware and software. To clearly illustrate this interchangeability of hardware and software, various illustrative components, blocks, modules, logic, circuits, and steps have been described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure. Also, the example fingerprint sensing system and/or mobile electronic device described herein may include components other than those shown, including well-known components.

Various techniques described herein may be implemented in hardware, software, firmware, or any combination thereof, unless specifically described as being implemented in a specific manner. Any features described as modules or components may also be implemented together in an integrated logic device or separately as discrete but interoperable logic devices. If implemented in software, the techniques may be realized at least in part by a non-transitory processor-readable storage medium comprising instructions that, when executed, perform one or more of the methods described herein. The non-transitory processor-readable data storage medium may form part of a computer program product, which may include packaging materials.

The non-transitory processor-readable storage medium may comprise random access memory (RAM) such as synchronous dynamic random access memory (SDRAM), read only memory (ROM), non-volatile random access memory (NVRAM), electrically erasable programmable read-only memory (EEPROM), FLASH memory, other known storage media, and the like. The techniques additionally, or alternatively, may be realized at least in part by a processor-readable communication medium that carries or communicates code in the form of instructions or data structures and that can be accessed, read, and/or executed by a computer or other processor.

Various embodiments described herein may be executed by one or more processors, such as one or more motion processing units (MPUs), sensor processing units (SPUs), host processor(s) or core(s) thereof, digital signal processors (DSPs), general purpose microprocessors, application specific integrated circuits (ASICs), application specific instruction set processors (ASIPs), field programmable gate arrays (FPGAs), a programmable logic controller (PLC), a complex programmable logic device (CPLD), a discrete gate or transistor logic, discrete hardware components, or any combination thereof designed to perform the functions described herein, or other equivalent integrated or discrete logic circuitry. The term "processor," as used herein may refer to any of the foregoing structures or any other structure suitable for implementation of the techniques described herein. As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Moreover, processors can exploit nano-scale architectures such as, but not limited to, molecular and quantum-dot based transistors, switches and gates, in order to optimize space usage or enhance performance of user equipment. A processor may also be implemented as a combination of computing processing units.

In addition, in some aspects, the functionality described herein may be provided within dedicated software modules or hardware modules configured as described herein. Also, the techniques could be fully implemented in one or more circuits or logic elements. A general purpose processor may be a microprocessor, but in the alternative, the processor may be any conventional processor, controller, microcontroller, or state machine. A processor may also be implemented as a combination of computing devices, e.g., a combination of an SPU/MPU and a microprocessor, a plurality of microprocessors, one or more microprocessors in conjunction with an SPU core, MPU core, or any other such configuration.

Overview of Discussion

Discussion begins with a description of an example piezoelectric micromachined ultrasonic transducer (PMUT), in accordance with various embodiments. Example arrays including PMUT devices are then described. Example operations of example arrays of ultrasonic transducers (e.g., PMUT devices) are then further described, including the use of multiple PMUT devices to form a beam for capturing a pixel. Examples of the detection of defective or degraded ultrasonic transducers are then described. Examples of correcting for identified defective or degraded ultrasonic transducers are then described.

Embodiments described herein provide a multiple step approach for handling defective or degraded ultrasonic transducers. In one embodiment, the system (e.g., ultrasonic fingerprint sensor or electronic device including an ultrasonic fingerprint sensor) monitors for a self-test condition, where the system monitors for any events that may lead to defective or degraded ultrasonic transducers. For example, shock events can be monitored using internal sensors, such as a motion sensor monitoring for mechanical shock events (e.g., the electronic device including the fingerprint sensor is dropped) and/or a temperature sensor for thermal shock events (e.g., temperature extremes likely to impact fingerprint sensor hardware). In one embodiment, images are captured during operation of the fingerprint sensor and compared to a stored image for determining whether pixel values are indicative of defective or degraded ultrasonic transducers. If such an event occurs, the fingerprint sensor may be notified that a self-test for determining whether there are any defective or degraded ultrasonic transducers should be initiated. In other embodiments, a self-test is performed on a regular basis (e.g., periodically, on device start up).

In accordance with various embodiments, defective or degraded ultrasonic transducer detection process is performed. An ultrasonic signal is generated at an ultrasonic sensing device comprising a plurality of ultrasonic transducers. A reflected ultrasonic signal corresponding to the ultrasonic signal is received at at least one ultrasonic transducer of the plurality of ultrasonic transducers. It is determined whether performance the at least one ultrasonic transducer is degraded based at least in part on the reflected ultrasonic signal. In one embodiment, a signal value for the reflected ultrasonic signal is determined. Provided the signal value is below or above a signal value threshold (e.g., does not satisfy the signal threshold value), the at least one ultrasonic transducer is classified as having degraded performance. In another embodiment, a time-of-flight for the at least one ultrasonic transducer is determined based at least on the ultrasonic signal and the reflected ultrasonic signal. In one embodiment, the time-of-flight for the at least one ultrasonic transducer is compared to the time-of-flight for proximate ultrasonic transducers. It should be appreciated that the time-of-flight can be compared to other values, e.g., a reference time-of-flight (ToF) value, or a previous determined time-of-flight value. Provided a difference between the time-of-flight for the at least one ultrasonic transducer and the time-of-flight for proximate ultrasonic transducers exceeds a time-of-flight difference threshold, the at least one ultrasonic transducer is classified as having degraded performance.

In further embodiments, corrective action is taken to handle defective or degraded ultrasonic transducers. If now defective or degraded ultrasonic transducers were present before, the correction may be initiated, or if defective or degraded ultrasonic transducers were already present, the correction process may be updated. In one embodiment, an image capture operation is initiated. During the image capture operation, the image capture operation is adjusted to account for the identification of defective ultrasonic transducers. In another embodiment, an image captured at the ultrasonic sensing device and an identification of defective ultrasonic transducers of the ultrasonic sensing device is received. Pixels of the image are corrected to account for the identification of defective ultrasonic transducers Piezoelectric Micromachined Ultrasonic Transducer (PMUT)

Systems and methods disclosed herein, in one or more aspects provide efficient structures for an acoustic transducer (e.g., a piezoelectric micromachined actuated transducer or PMUT). One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. In addition, the word "example" is used herein to mean serving as an example, instance, or illustration.

FIG. 1A is a diagram illustrating a PMUT device 100 having a center pinned membrane, according to some embodiments. PMUT device 100 includes an interior pinned membrane 120 positioned over a substrate 140 to define a cavity 130. In one embodiment, membrane 120 is attached both to a surrounding edge support 102 and interior support 104. In one embodiment, edge support 102 is connected to an electric potential. Edge support 102 and interior support 104 may be made of electrically conducting materials, such as and without limitation, aluminum, molybdenum, or titanium. Edge support 102 and interior support 104 may also be made of dielectric materials, such as silicon dioxide, silicon nitride or aluminum oxide that have electrical connections on the sides or in vias through edge support 102 or interior support 104, electrically coupling lower electrode 106 to electrical wiring in substrate 140.

In one embodiment, both edge support 102 and interior support 104 are attached to a substrate 140. In various embodiments, substrate 140 may include at least one of, and without limitation, silicon or silicon nitride. It should be appreciated that substrate 140 may include electrical wirings and connection, such as aluminum or copper. In one embodiment, substrate 140 includes a CMOS logic wafer bonded to edge support 102 and interior support 104. In one embodiment, the membrane 120 comprises multiple layers. In an example embodiment, the membrane 120 includes lower electrode 106, piezoelectric layer 110, and upper electrode 108, where lower electrode 106 and upper electrode 108 are coupled to opposing sides of piezoelectric layer 110. As shown, lower electrode 106 is coupled to a lower surface of piezoelectric layer 110 and upper electrode 108 is coupled to an upper surface of piezoelectric layer 110. It should be appreciated that, in various embodiments, PMUT device 100 is a microelectromechanical (MEMS) device.

In one embodiment, membrane 120 also includes a mechanical support layer 112 (e.g., stiffening layer) to mechanically stiffen the layers. In various embodiments, mechanical support layer 112 may include at least one of, and without limitation, silicon, silicon oxide, silicon nitride, aluminum, molybdenum, titanium, etc. In one embodiment, PMUT device 100 also includes an acoustic coupling layer 114 above membrane 120 for supporting transmission of acoustic signals. It should be appreciated that acoustic coupling layer can include air, liquid, gel-like materials, epoxy, or other materials for supporting transmission of acoustic signals. In one embodiment, PMUT device 100 also includes platen layer 116 above acoustic coupling layer 114 for containing acoustic coupling layer 114 and providing a contact surface for a finger or other sensed object with PMUT device 100. It should be appreciated that, in various embodiments, acoustic coupling layer 114 provides a contact surface, such that platen layer 116 is optional. Moreover, it should be appreciated that acoustic coupling layer 114 and/or platen layer 116 may be included with or used in conjunction with multiple PMUT devices. For example, an array of PMUT devices may be coupled with a single acoustic coupling layer 114 and/or platen layer 116.

Figure 1B:
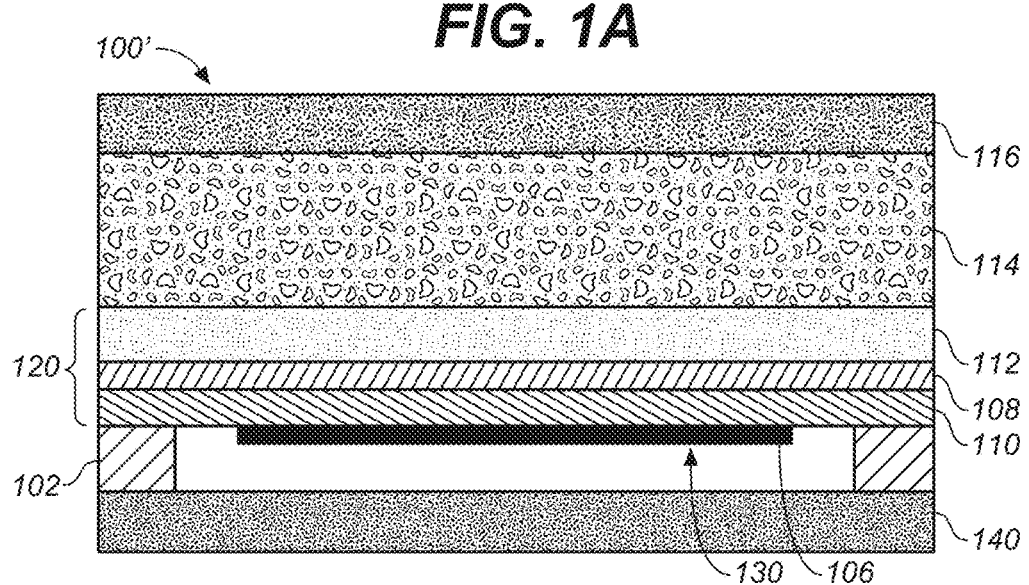
FIG. 1B is a diagram illustrating a PMUT device having an unpinned membrane, according to some embodiments.

FIG. 1B is identical to FIG. 1A in every way, except that the PMUT device 100' of FIG. 1B omits the interior support 104 and thus membrane 120 is not pinned (e.g., is "unpinned"). There may be instances in which an unpinned membrane 120 is desired. However, in other instances, a pinned membrane 120 may be employed.

Figure 2:
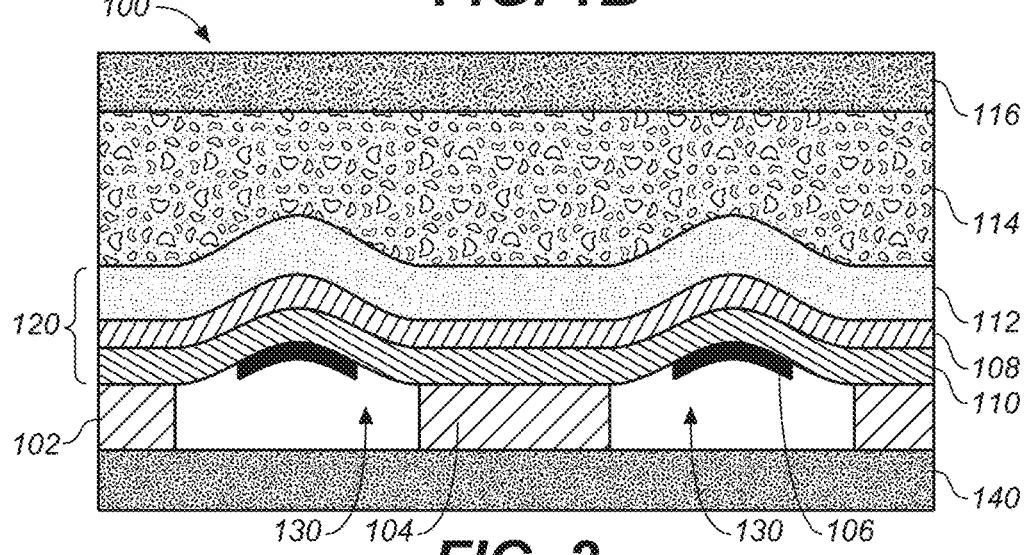
FIG. 2 is a diagram illustrating an example of membrane movement during activation of a PMUT device, according to some embodiments.

FIG. 2 is a diagram illustrating an example of membrane movement during activation of PMUT device 100, according to some embodiments. As illustrated with respect to FIG. 2, in operation, responsive to an object proximate platen layer 116, the electrodes 106 and 108 deliver a high frequency electric charge to the piezoelectric layer 110, causing those portions of the membrane 120 not pinned to the surrounding edge support 102 or interior support 104 to be displaced upward into the acoustic coupling layer 114. This generates a pressure wave that can be used for signal probing of the object. Return echoes can be detected as pressure waves causing movement of the membrane, with compression of the piezoelectric material in the membrane causing an electrical signal proportional to amplitude of the pressure wave.

The described PMUT device 100 can be used with almost any electrical device that converts a pressure wave into mechanical vibrations and/or electrical signals. In one aspect, the PMUT device 100 can comprise an acoustic sensing element (e.g., a piezoelectric element) that generates and senses ultrasonic sound waves. An object in a path of the generated sound waves can create a disturbance (e.g., changes in frequency or phase, reflection signal, echoes, etc.) that can then be sensed. The interference can be analyzed to determine physical parameters such as (but not limited to)distance, density and/or speed of the object. As an example, the PMUT device 100 can be utilized in various applications, such as, but not limited to, fingerprint or physiologic sensors suitable for wireless devices, industrial systems, automotive systems, robotics, telecommunications, security, medical devices, etc. For example, the PMUT device 100 can be part of a sensor array comprising a plurality of ultrasonic transducers deposited on a wafer, along with various logic, control and communication electronics. A sensor array may comprise homogenous or identical PMUT devices 100, or a number of different or heterogonous device structures.

In various embodiments, the PMUT device 100 employs a piezoelectric layer 110, comprised of materials such as, but not limited to, aluminum nitride (AlN), scandium doped aluminum nitride (ScAlN), lead zirconate titanate (PZT), quartz, polyvinylidene fluoride (PVDF), and/or zinc oxide, to facilitate both acoustic signal production and sensing. The piezoelectric layer 110 can generate electric charges under mechanical stress and conversely experience a mechanical strain in the presence of an electric field. For example, the piezoelectric layer 110 can sense mechanical vibrations caused by an ultrasonic signal and produce an electrical charge at the frequency (e.g., ultrasonic frequency) of the vibrations. Additionally, the piezoelectric layer 110 can generate an ultrasonic wave by vibrating in an oscillatory fashion that might be at the same frequency (e.g., ultrasonic frequency) as an input current generated by an alternating current (AC) voltage applied across the piezoelectric layer 110. It should be appreciated that the piezoelectric layer 110 can include almost any material (or combination of materials) that exhibits piezoelectric properties, such that the structure of the material does not have a center of symmetry and a tensile or compressive stress applied to the material alters the separation between positive and negative charge sites in a cell causing a polarization at the surface of the material. The polarization is directly proportional to the applied stress and is direction dependent so that compressive and tensile stresses results in electric fields of opposite polarizations.

Figure 10:
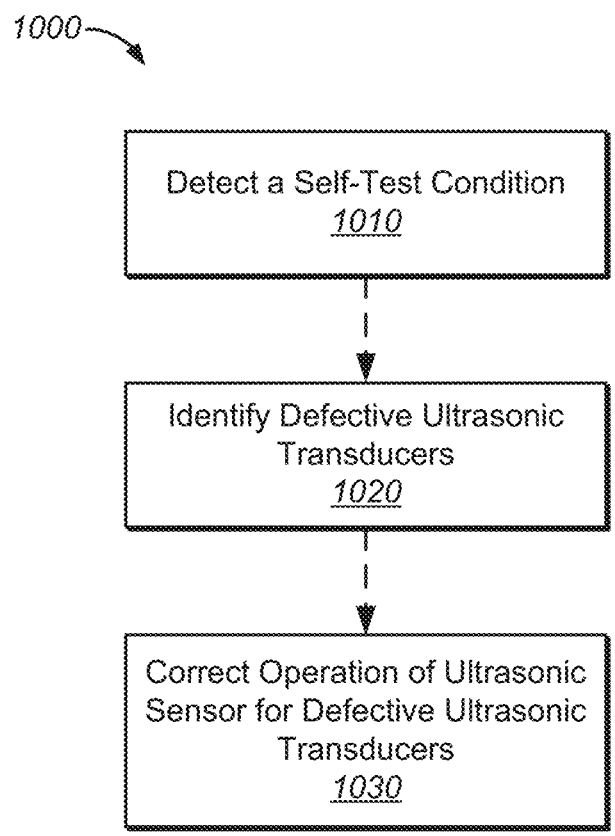
FIG. 10 illustrates a flow diagram of an example method for detection and correction for defective or degraded ultrasonic transducers of an ultrasonic fingerprint sensor, according to embodiments.

Further, the PMUT device 100 comprises electrodes 106 and 108 that supply and/or collect the electrical charge to/from the piezoelectric layer 110. It should be appreciated that electrodes 106 and 108 can be continuous and/or patterned electrodes (e.g., in a continuous layer and/or a patterned layer). For example, as illustrated, electrode 106 is a patterned electrode and electrode 108 is a continuous electrode. As an example, electrodes 106 and 108 can be comprised of almost any metal layers, such as, but not limited to, Aluminum (Al)/Titanium (Ti), Molybdenum (Mo), etc., which are coupled with and on opposing sides of the piezoelectric layer 110. In one embodiment, PMUT device also includes a third electrode, as illustrated in FIG. 10 and described below.

According to an embodiment, the acoustic impedance of acoustic coupling layer 114 is selected to be similar to the acoustic impedance of the platen layer 116, such that the acoustic wave is efficiently propagated to/from the membrane 120 through acoustic coupling layer 114 and platen layer 116. As an example, the platen layer 116 can comprise various materials having an acoustic impedance in the range between 0.8 to 4 MRayl, such as, but not limited to, plastic, resin, rubber, Teflon, epoxy, etc. In another example, the platen layer 116 can comprise various materials having a high acoustic impedance (e.g., an acoustic impendence greater than 10 MiRayl), such as, but not limited to, glass, aluminum-based alloys, sapphire, etc. Typically, the platen layer 116 can be selected based on an application of the sensor. For instance, in fingerprinting applications, platen layer 116 can have an acoustic impedance that matches (e.g., exactly or approximately) the acoustic impedance of human skin (e.g., $1.6 \times 10^6$Rayl). Further, in one aspect, the platen layer 116 can further include a thin layer of anti-scratch material. In various embodiments, the anti-scratch layer of the platen layer 116 is less than the wavelength of the acoustic wave that is to be generated and/or sensed to provide minimum interference during propagation of the acoustic wave. As an example, the anti-scratch layer can comprise various hard and scratch-resistant materials (e.g., having a Mohs hardness of over 7 on the Mohs scale), such as, but not limited to sapphire, glass, MN, Titanium nitride (TiN), Silicon carbide (SiC), diamond, etc. As an example, PMUT device 100 can operate at 20 MHz and accordingly, the wavelength of the acoustic wave propagating through the acoustic coupling layer 114 and platen layer 116 can be 70-150 microns. In this example scenario, insertion loss can be reduced and acoustic wave propagation efficiency can be improved by utilizing an anti-scratch layer having a thickness of 1 micron and the platen layer 116 as a whole having a thickness of 1-2 millimeters. It is noted that the term "anti-scratch material" as used herein relates to a material that is resistant to scratches and/or scratch-proof and provides substantial protection against scratch marks.

In accordance with various embodiments, the PMUT device 100 can include metal layers (e.g., Aluminum (Al)/Titanium (Ti), Molybdenum (Mo), etc.) patterned to form electrode 106 in particular shapes (e.g., ring, circle, square, octagon, hexagon, etc.) that are defined in-plane with the membrane 120. Electrodes can be placed at a maximum strain area of the membrane 120 or placed at close to either or both the surrounding edge support 102 and interior support 104. Furthermore, in one example, electrode 108 can be formed as a continuous layer providing a ground plane in contact with mechanical support layer 112, which can be formed from silicon or other suitable mechanical stiffening material. In still other embodiments, the electrode 106 can be routed along the interior support 104, advantageously reducing parasitic capacitance as compared to routing along the edge support 102.

For example, when actuation voltage is applied to the electrodes, the membrane 120 will deform and move out of plane. The motion then pushes the acoustic coupling layer 114 it is in contact with and an acoustic (ultrasonic) wave is generated. Oftentimes, vacuum is present inside the cavity 130 and therefore damping contributed from the media within the cavity 130 can be ignored. However, the acoustic coupling layer 114 on the other side of the membrane 120 can substantially change the damping of the PMUT device 100. For example, a quality factor greater than 20 can be observed when the PMUT device 100 is operating in air with atmosphere pressure (e.g., acoustic coupling layer 114 is air) and can decrease lower than 2 if the PMUT device 100 is operating in water (e.g., acoustic coupling layer 114 is water).

Figure 3:
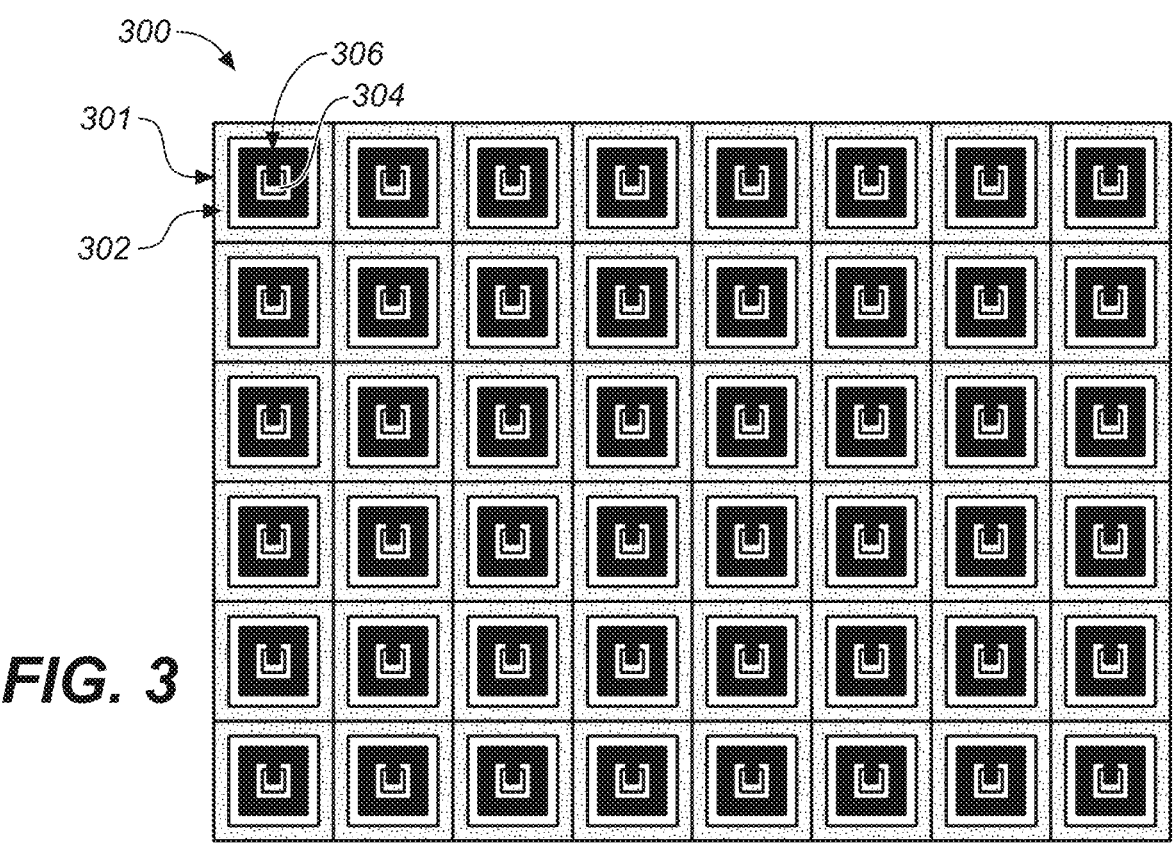
FIG. 3 illustrates an example array of square-shaped PMUT devices, according to some embodiments.

FIG. 3 illustrates an example two-dimensional array 300 of square-shaped PMUT devices 301 formed from PMUT devices having a substantially square shape similar to that discussed in conjunction with FIGS. 1, 2 and 3. Layout of square surrounding edge support 302, interior support 304, and square-shaped lower electrode 306 surrounding the interior support 304 are illustrated, while other continuous layers are not shown for clarity. As illustrated, array 300 includes columns of square-shaped PMUT devices 301 that are in rows and columns. It should be appreciated that rows or columns of the square-shaped PMUT devices 301 may be offset. Moreover, it should be appreciated that square-shaped PMUT devices 301 may contact each other or be spaced apart. In various embodiments, adjacent square-shaped PMUT devices 301 are electrically isolated. In other embodiments, groups of adjacent square-shaped PMUT devices 301 are electrically connected, where the groups of adjacent square-shaped PMUT devices 301 are electrically isolated.

In operation, during transmission, selected sets of PMUT devices in the two-dimensional array can transmit an acoustic signal (e.g., a short ultrasonic pulse) and during sensing, the set of active PMUT devices in the two-dimensional array can detect an interference of the acoustic signal with an object (in the path of the acoustic wave). The received interference signal (e.g., generated based on reflections, echoes, etc. of the acoustic signal from the object) can then be analyzed. As an example, an image of the object, a distance of the object from the sensing component, a density of the object, a motion of the object, etc., can all be determined based on comparing a frequency and/or phase of the interference signal with a frequency and/or phase of the acoustic signal. Moreover, results generated can be further analyzed or presented to a user via a display device (not shown).

Figure 4:
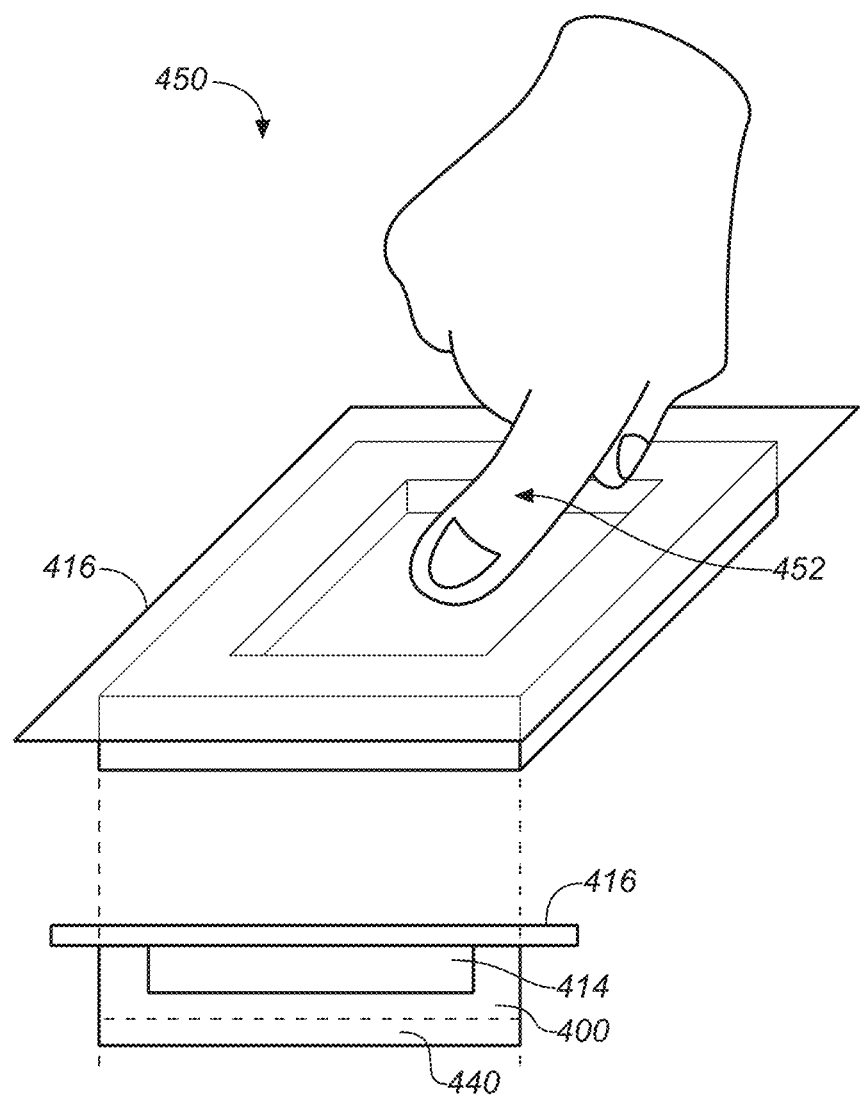
FIG. 4 illustrates a PMUT array used in an ultrasonic fingerprint sensing system, according to some embodiments.

FIG. 4 illustrates an embodiment of a PMUT array used in an ultrasonic fingerprint sensing system 450. The fingerprint sensing system 450 can include a platen 416 onto which a human finger 452 may make contact. Ultrasonic signals are generated and received by a PMUT device array 400, and travel back and forth through acoustic coupling layer 414 and platen 416. Signal analysis is conducted using processing logic module 440 (e.g., control logic) directly attached (via wafer bonding or other suitable techniques) to the PMUT device array 400. It will be appreciated that the size of platen 416 and the other elements illustrated in FIG. 4 may be much larger (e.g., the size of a handprint) or much smaller (e.g., just a fingertip) than as shown in the illustration, depending on the particular application.

In this example for fingerprinting applications, the human finger 452 and the processing logic module 440 can determine, based on a difference in interference of the acoustic signal with valleys and/or ridges of the skin on the finger, an image depicting epi-dermis and/or dermis layers of the finger. Further, the processing logic module 440 can compare the image with a set of known fingerprint images to facilitate identification and/or authentication. Moreover, in one example, if a match (or substantial match) is found, the identity of user can be verified. In another example, if a match (or substantial match) is found, a command/operation can be performed based on an authorization rights assigned to the identified user. In yet another example, the identified user can be granted access to a physical location and/or network/computer resources (e.g., documents, files, applications, etc.)

In another example, for finger-based applications, the movement of the finger can be used for cursor tracking/movement applications. In such embodiments, a pointer or cursor on a display screen can be moved in response to finger movement. It is noted that processing logic module 440 can include or be connected to one or more processors configured to confer at least in part the functionality of system 450. To that end, the one or more processors can execute code instructions stored in memory, for example, volatile memory and/or nonvolatile memory.

The example embodiments described in FIG. 1 through FIG. 4 illustrate the fingerprint sensing system including a platen layer 116 where the user places his or her finger (e.g., contact surface), where platen layer 116 is coupled with the ultrasonic transducers through acoustic coupling layer 114. The fingerprint sensing system may also be incorporated into other devices, where the platen layer 116 and acoustic coupling layer 114 may be replaced by one or more other layers, depending on the device. For example, the fingerprint sensing device may be incorporated in a display, such as an Organic Light-Emitting Diode (OLED) display. In this case, acoustic coupling layer 114 and platen layer 116 are replaced by the various layers of the display.

Example Operation of a Two-Dimensional Array of Ultrasonic Transducers

Systems and methods disclosed herein, in one or more aspects provide for the operation of a two-dimensional array of ultrasonic transducers (e.g., an array of piezoelectric micromachined actuated transducers or PMUTs). One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details. In other instances, well-known structures and devices are shown in block diagram form in order to facilitate describing the embodiments in additional detail.

Figure 5:
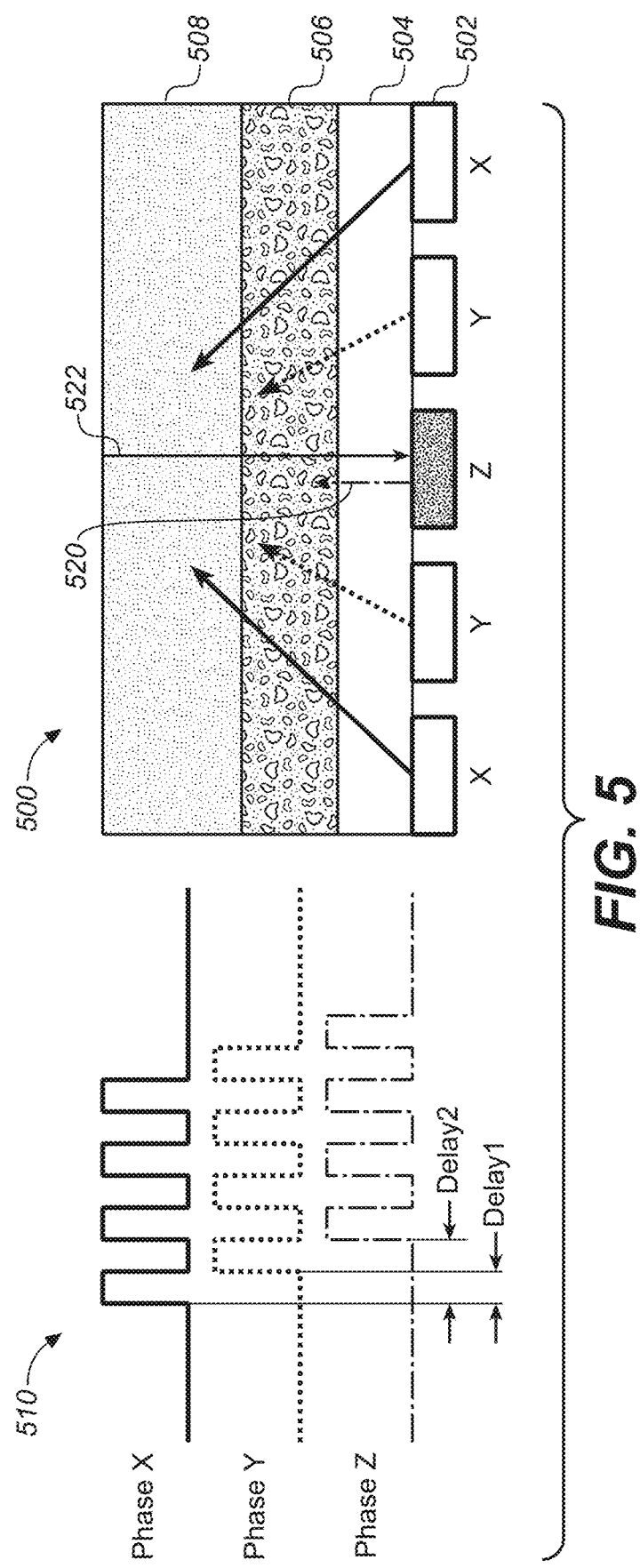
FIG. 5 illustrates an example ultrasonic transducer system with phase delayed transmission, according to some embodiments.

FIG. 5 illustrates an example ultrasonic transducer system 500 with phase delayed transmission, according to some embodiments. As illustrated, FIG. 5 shows ultrasonic beam transmission and reception using a one-dimensional, five-element, ultrasonic transducer system 500 having phase delayed inputs 510. In various embodiments, ultrasonic transducer system 500 is comprised of PMUT devices having a center pinned membrane (e.g., PMUT device 100 of FIG. 1A).

As illustrated, ultrasonic transducer system 500 includes five ultrasonic transducers 502 including a piezoelectric material and activating electrodes that are covered with a continuous stiffening layer 504 (e.g., a mechanical support layer). Stiffening layer 504 contacts acoustic coupling layer 506, and in turn is covered by a platen layer 508. In various embodiments, the stiffening layer 504 can be silicon, and the platen layer 508 formed from metal, glass, sapphire, or polycarbonate or similar durable plastic. The intermediately positioned acoustic coupling layer 506 can be formed from a plastic or gel such as polydimethylsiloxane (PDMS), epoxy, or other material. In one embodiment, the material of acoustic coupling layer 506 has an acoustic impedance selected to be between the acoustic impedance of layers 504 and 508. In one embodiment, the material of acoustic coupling layer 506 has an acoustic impedance selected to be close the acoustic impedance of platen layer 508, to reduce unwanted acoustic reflections and improve ultrasonic beam transmission and sensing. However, alternative material stacks to the one shown in FIG. 5 may be used and certain layers may be omitted, provided the medium through which transmission occurs passes signals in a predictable way.

In operation, and as illustrated in FIG. 5, the ultrasonic transducers 502 labelled with an "x" are triggered to emit ultrasonic waves at an initial time. At a second time, (e.g., 1-100 nanoseconds later), the ultrasonic transducers 502 labelled with a "y" are triggered. At a third time (e.g., 1-100 nanoseconds after the second time) the ultrasonic transducer 502 labelled with a "z" is triggered. The ultrasonic waves transmitted at different times cause interference with each other, effectively resulting in a single high intensity beam 520 that exits the platen layer 508, contacts objects, such as a finger (not shown), that contact the platen layer 508, and is in part reflected back to the ultrasonic transducers. In one embodiment, the ultrasonic transducers 502 are switched from a transmission mode to a reception mode, allowing the "z" ultrasonic transducer to detect any reflected signals. In other words, the phase delay pattern of the ultrasonic transducers 502 is symmetric about the focal point where high intensity beam 520 exits platen layer 508.

It should be appreciated that an ultrasonic transducer 502 of ultrasonic transducer system 500 may be used to transmit and/or receive an ultrasonic signal, and that the illustrated embodiment is a non-limiting example. The received signal 522 (e.g., generated based on reflections, echoes, etc. of the acoustic signal from an object contacting or near the platen layer 508) can then be analyzed. As an example, an image of the object, a distance of the object from the sensing component, acoustic impedance of the object, a motion of the object, etc., can all be determined based on comparing a frequency, amplitude and/or phase of the received interference signal with a frequency, amplitude and/or phase of the transmitted acoustic signal. Moreover, results generated can be further analyzed or presented to a user via a display device (not shown).

Figure 6:
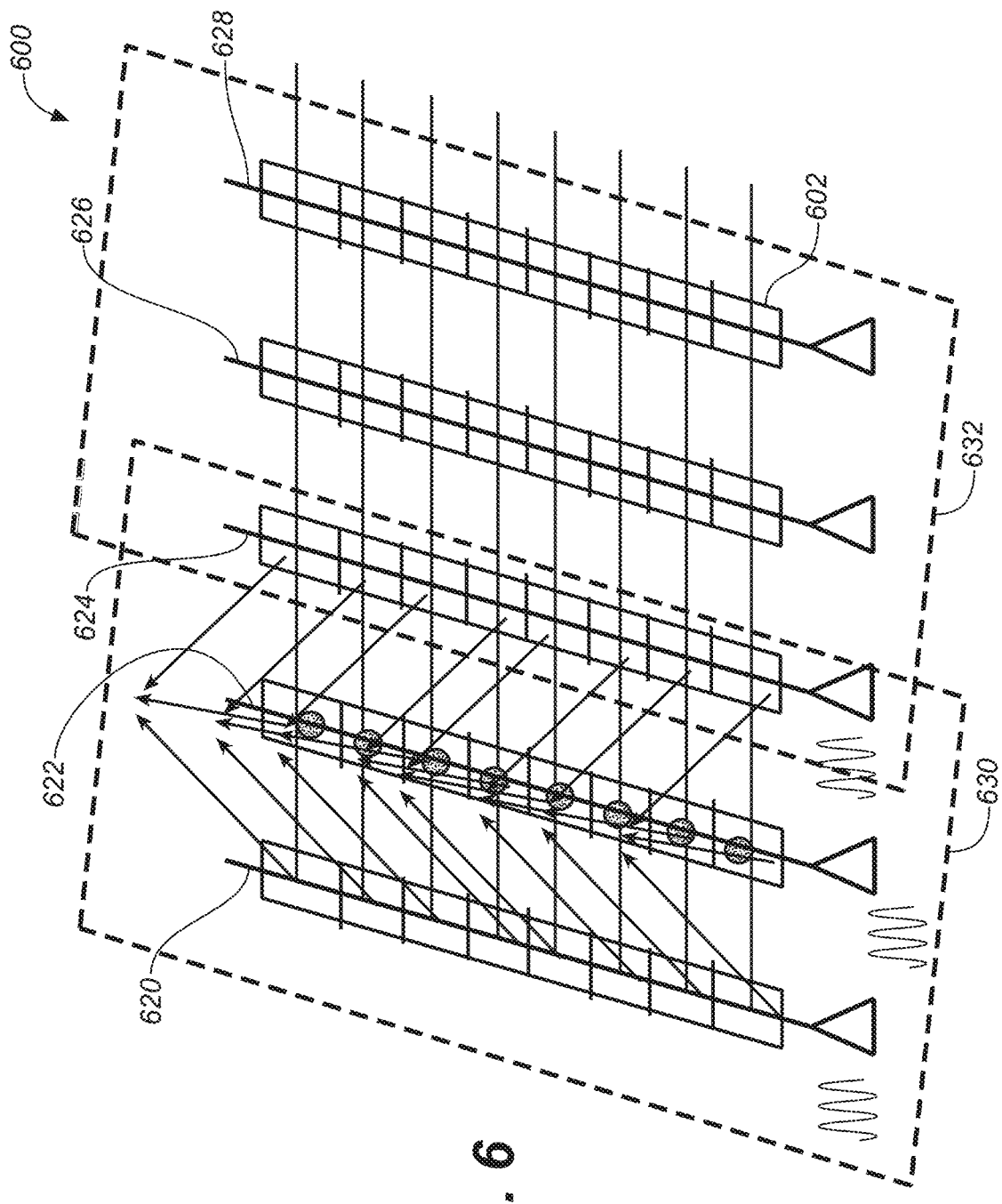
FIG. 6 illustrates another example ultrasonic transducer system with phase delayed transmission, according to some embodiments.

FIG. 6 illustrates another example ultrasonic transducer system 600 with phase delayed transmission, according to some embodiments. As illustrated, FIG. 6 shows ultrasonic beam transmission and reception using a virtual block of two-dimensional, 24-element, ultrasonic transducers that form a subset of a 40-element ultrasonic transducer system 600 having phase delayed inputs. In operation, an array position 630 (represented by the dotted line), also referred to herein as a virtual block, includes columns 620, 622 and 624 of ultrasonic transducers 602. At an initial time, columns 620 and 624 of array position 630 are triggered to emit ultrasonic waves at an initial time. At a second time (e.g., several nanoseconds later), column 622 of array position 630 is triggered. The ultrasonic waves interfere with each other, substantially resulting in emission of a high intensity ultrasonic wave centered on column 622. In one embodiment, the ultrasonic transducers 602 in columns 620 and 624 are switched off, while column 622 is switched from a transmission mode to a reception mode, allowing detection of any reflected signals.

In one embodiment, after the activation of ultrasonic transducers 602 of array position 630, ultrasonic transducers 602 of another array position 632, comprised of columns 624, 626, and 628 of ultrasonic transducers 602 are triggered in a manner similar to that described in the foregoing description of array position 630. In one embodiment, ultrasonic transducers 602 of another array position 632 are activated after a detection of a reflected ultrasonic signal at column 622 of array position 630. It should be appreciated that while movement of the array position by two columns of ultrasonic transducers is illustrated, movement by one, three, or more columns rightward or leftward is contemplated, as is movement by one or more rows, or by movement by both some determined number of rows and columns. In various embodiments, successive array positions can be either overlapping in part, or can be distinct. In some embodiments the size of array positions can be varied. In various embodiments, the number of ultrasonic transducers 602 of an array position for emitting ultrasonic waves can be larger than the number of ultrasonic transducers 602 of an array position for ultrasonic reception. In still other embodiments, array positions can be square, rectangular, ellipsoidal, circular, or more complex shapes such as crosses.

Figures 7A, 7B:
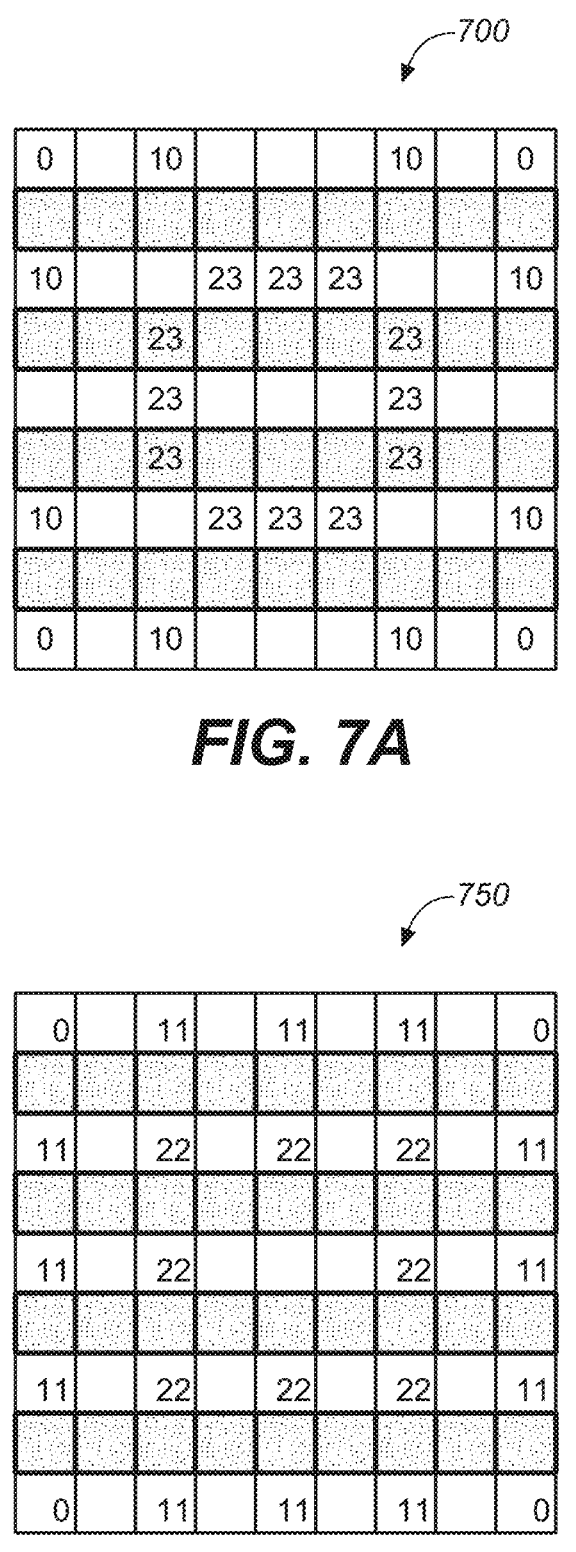

FIG. 7A illustrates an example phase delay pattern for ultrasonic signal transmission of a 9×9 ultrasonic transducer block 700 of a two-dimensional array of ultrasonic transducers, according to some embodiments. As illustrated in FIG. 7A, each number in the ultrasonic transducer array is equivalent to the nanosecond delay used during operation, and an empty element (e.g., no number) in the ultrasonic transducer block 700 means that an ultrasonic transducer is not activated for signal transmission during operation. In various embodiments, ultrasonic wave amplitude can be the same or similar for each activated ultrasonic transducer, or can be selectively increased or decreased relative to other ultrasonic transducers. In the illustrated pattern, initial ultrasonic transducer activation is limited to corners of ultrasonic transducer block 700, followed 10 nanoseconds later by a rough ring around the edges of ultrasonic transducer block 700. After 23 nanoseconds, an interior ring of ultrasonic transducers is activated. Together, the twenty-four activated ultrasonic transducers generate an ultrasonic beam centered on the ultrasonic transducer block 700. In other words, the phase delay pattern of ultrasonic transducer block 700 is symmetric about the focal point where a high intensity beam contacts an object.

It should be appreciated that different ultrasonic transducers of ultrasonic transducer block 700 may be activated for receipt of reflected ultrasonic signals. For example, the center 3×3 ultrasonic transducers of ultrasonic transducer block 700 may be activated to receive the reflected ultrasonic signals. In another example, the ultrasonic transducers used to transmit the ultrasonic signal are also used to receive the reflected ultrasonic signal. In another example, the ultrasonic transducers used to receive the reflected ultrasonic signals include at least one of the ultrasonic transducers also used to transmit the ultrasonic signals.

FIG. 7B illustrates another example phase delay pattern for a 9×9 ultrasonic transducer block 800, according to some embodiments. As illustrated in FIG. 7B, the example phase delay pattern utilizes equidistant spacing of transmitting ultrasonic transducers. As illustrated in FIG. 7A, each number in the ultrasonic transducer array is equivalent to the nanosecond delay used during operation, and an empty element (e.g., no number) in the ultrasonic transducer block 750 means that an ultrasonic transducer is not activated for signal transmission during operation. In the illustrated embodiment, the initial ultrasonic transducer activation is limited to corners of ultrasonic transducer block 750, followed 11 nanoseconds later by a rough ring around the edges of ultrasonic transducer block 750. After 22 nanoseconds, an interior ring of ultrasonic transducers is activated. The illustrated embodiment utilizes equidistant spacing of the transmitting ultrasonic transducers to reduce issues with crosstalk and heating, wherein each activated ultrasonic transducers is surrounded by un-activated ultrasonic transducers. Together, the twenty-four activated ultrasonic transducers generate an ultrasonic beam centered on the ultrasonic transducer block 750.

Figure 8:
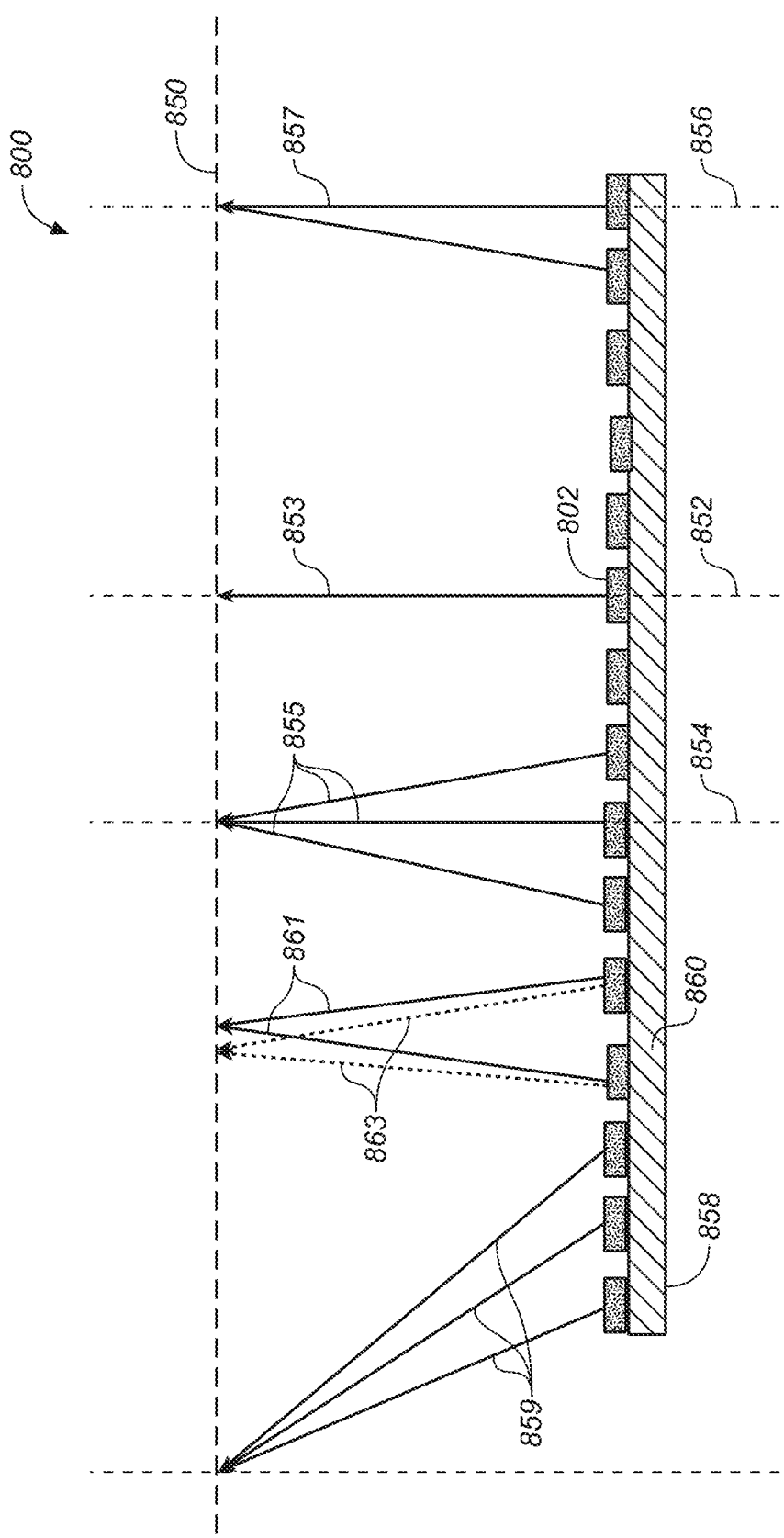
FIG. 8 illustrates an example ultrasonic transducer system with phase delayed transmission, according to some embodiments.

FIG. 8 illustrates an example ultrasonic transducer system 800 with phase delayed transmission, according to some embodiments. FIG. 8 shows five different modes of ultrasonic beam transmission using an example one-dimensional, fifteen-element, ultrasonic transducer system 800 having phase delayed inputs. As illustrated, ultrasonic transducers 802 can be operated in various modes to provide ultrasonic beam spots focused along line 850 (e.g., a top of a platen layer). In a first mode, a single ultrasonic transducer 852 is operated to provide a single broad ultrasonic beam having a peak amplitude centered on arrow 853. In a second mode, multiple ultrasonic transducers in a symmetrical pattern 854 about the center ultrasonic transducer are sequentially triggered to emit ultrasonic waves at differing initial times. As illustrated, a center located transducer is triggered at a delayed time with respect to surrounding transducers (which are triggered simultaneously). The ultrasonic waves interfere with each other, resulting in a single high intensity beam 855. In a third mode, for ultrasonic transducers 856 located adjacent to or near an edge of the ultrasonic transducer system 800, an asymmetrical triggering pattern can be used to produce beam 857. In a fourth mode, asymmetrical triggering patterns for transducers 858 can be used to steer an ultrasound beam to an off-center location 859. A shown, the focused beam 859 can be directed to a point above and outside boundaries of the ultrasonic transducer system 800. In a fifth mode, the beam can be steered to focus at a series of discrete positions, with the beam spacing having a pitch less than, equal to, or greater than a pitch of the ultrasonic transducers. In FIG. 8, transducers 860 are triggered at separate times to produce beam spots separated by a pitch less than that of the ultrasonic transducers (indicated respectively by solid lines directed to form beam spot 861 and dotted lines to form beam spot 863).

Example Operation of a Fingerprint Sensor Comprised of Ultrasonic Transducers

Various embodiments described herein provide for the detection of and/or correction for defective ultrasonic transducers of an ultrasonic fingerprint sensor. In some embodiments, the ultrasonic fingerprint sensor provides a number of different modes of operation. For example, in some embodiments, a fingerprint sensor is configured to provide different modes for finger detection. If a finger's presence is detected on the fingerprint sensor, in one embodiment, the system will exit the finger detection mode in order to capture the fingerprint image. Embodiments described herein provide for a finger detection mode that minimizes the number of false rejects and minimizes power consumption of the fingerprint sensor. In finger detection mode, a false reject is defined as failing to recognize that a finger is present on the sensor when a finger is in fact interacting with the fingerprint sensor. False rejects are viewed as catastrophic failures in finger detection mode, because they could prevent a user from turning on the device. False accepts (e.g., the fingerprint sensor detects a finger when no finger is present) increase the average power consumption of the system because the fingerprint sensor and associated processor activate to do a full fingerprint scan even though no finger is present. As a result, minimizing false accepts is related to minimizing power consumption. Moreover, it should be understood that defective or degraded ultrasonic transducers can have a significant impact on the operation of finger detection. For example, in a first finder detection mode, very few ultrasonic transducers may be activated to capture a pixel. If one or more ultrasonic transducers used for the pixel capture are defective, the performance of the finger detection operation may be negatively impacted, causing an incorrect result.

Figure 9:
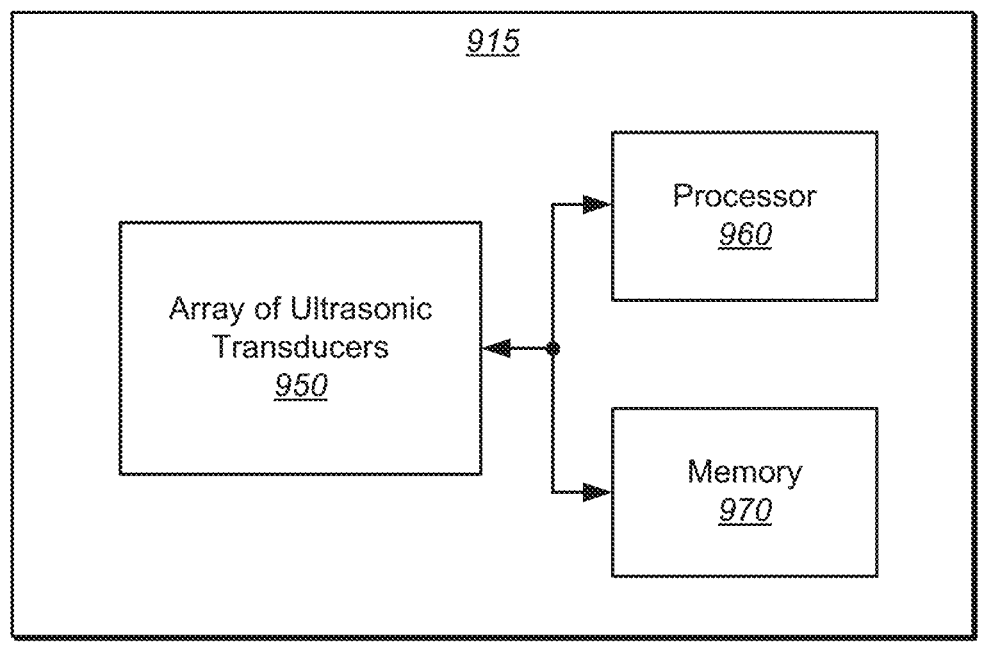
FIG. 9 illustrates an example fingerprint sensor, in accordance with various embodiments.

FIG. 9 illustrates an example fingerprint sensor 915, in accordance with various embodiments. In one embodiment, fingerprint sensor 915 includes an array 950 of ultrasonic transducers (e.g., PMUT devices), a processor 960, and a memory 970. In various embodiments, processor 960 performs certain operations in accordance with instructions stored within memory 970. It should be appreciated that components of fingerprint sensor 915 are examples, and that certain components, such as processor 960 and/or memory 970 may not be located within fingerprint sensor 915. For example, system circuitry of an electronic device including fingerprint sensor 915 may include a processor and/or memory for performing certain operations.

In one embodiment, fingerprint sensor 915 includes processor 960 for performing the pixel capture, where pixel capture is performed using subsets of ultrasonic transducers (e.g., PMUTs) of fingerprint sensor 915. In other embodiments, processor 960 can perform at least some signal analysis, e.g., thresholding, to determine whether an object has interacted with fingerprint sensor 915. In other embodiments, processor 960 can analyze captured pixels and determine whether the object has characteristics of finger, e.g., a pattern resembling the ridge/valley pattern of a fingerprint. In other embodiments, processor 960 can capture an image of the fingerprint and forward it to a processor of system circuitry for further analysis.

While the embodiment of FIG. 9 includes processor 960 and memory 970, as described above, it should be appreciated that various functions of processor 960 and memory 970 may reside in other components of the electronic device within which fingerprint sensor 915 resides (e.g., within always-on circuitry or system circuitry). Moreover, it should be appreciated that processor 960 may be any type of processor for performing any portion of the described functionality (e.g., custom digital logic).

In various embodiments, a power supply can energize at least a portion of the system circuitry according with trigger signaling (or other type of control signal) provided (e.g., generated and transmitted) by the always-on circuitry. For example, the system circuitry can include a power controller that can receive trigger signaling (e.g., a control instruction) and, in response, can energize at least one processor of the system circuitry from a power-save state to a full-power state. The at least one processor that transitions from the power-save state to the full power state can execute one or more analyses in order to analyze features (e.g., fingerprints) of an image of a fingerprint from the fingerprint sensor 915 that triggered the trigger signaling. In various embodiments, the analysis of the image of a fingerprint can include computer-accessible instruction (e.g., computer-readable instructions and/or computer-executable instructions) that in response to execution by a processor can permit or otherwise facilitate the electronic device to implement a defined algorithm (or process) for fingerprint identification or analysis.

In various embodiments, fingerprint sensor 915 can include ultrasonic transducers (e.g., PMUTs) able to generate and detect acoustic/pressure waves. Examples of PMUT devices and arrays of PMUT devices are described in accordance with FIGS. 1-8 above. In embodiments, a device includes fingerprint sensor 915 comprised of an array of ultrasonic transducers that can facilitate ultrasonic signal generation and sensing. For example, fingerprint sensor 915 can include a silicon wafer having a two-dimensional (or one-dimensional) array of ultrasonic transducers.

In some embodiment, the electronic device within which fingerprint sensor 915 resides includes always-on circuitry that can be energized or otherwise power-on continuously or nearly continuously and can be configured to monitor touch of fingerprint sensor 915. In addition, in response to human touch (e.g., touch by a human finger or other human body part), the always-on circuitry can be further configured to trigger detection and/or another type of analysis of elements of the human touch or a human body associated therewith. To at least that end, the always-on circuitry can be configured to implement a first phase of a finger detection mode (also referred to as FDMA). The always-on circuitry can also be configured to implement a second phase of a finger detection mode (also referred to as FDMB) and/or a third phase of a finger detection mode (also referred to as FDMC). It should be appreciated that successive phases of finger detection include activation of successively larger numbers of ultrasonic transducers. It should be appreciated that always-on circuitry can implement any phase of the finger detection mode independently, in any combination, or in any order.

Example Detection of and Correction for Defective Ultrasonic Transducer in an Ultrasonic Sensor Ultrasonic fingerprint sensors typically include a plurality of ultrasonic transducers, e.g., a two-dimensional array of ultrasonic transducers, to capture an image of a fingerprint. Accordingly, accuracy of captured images is essential to the performance of image matching for user authentication. Individual ultrasonic transducers of ultrasonic fingerprint sensors may be degraded or defective, impacting the quality of the captured image and thereby possibly impacting the user authentication. For example, at manufacture, some ultrasonic transducers can be degraded or defective, or during usage, a shock event (temperature shock or mechanical shock) may cause one or more ultrasonic transducers to fail.

A defective or degraded ultrasonic transducer may produce a constant response or no response to an input signal. These ultrasonic transducers can cause fixed patterns in the image that can create problems in authenticating the user. Embodiments described herein provide for the detection of defective or degraded ultrasonic transducers. Other embodiments described herein provide for the amelioration of the defective or degraded ultrasonic transducers, for mitigating the effect of these ultrasonic transducers on the image generation.

With reference to FIGS. 1A and 1B, example structures of ultrasonic transducers of an ultrasonic fingerprint sensor are illustrated. FIG. 3 illustrates an example two-dimensional array of ultrasonic transducers. Defective or degraded (e.g., dead) ultrasonic transducers pixels may be present in an ultrasonic sensor. For example, immediately after manufacturing defects may be caused due to issues in the semiconductor manufacturing process. Other kind of defects could also be introduced by issues in the process of making the sensor module and attaching the sensor to (cover) materials such as glass or metal for use in a final product such as a mobile phone. For example, if there is an air bubble or impurity in the glass, adhesive layer, or the epoxy layer, this would result in a region of no-signal in the image because the acoustic waves would get reflected on the bubble/impurity before reaching the user's finger. While the ultrasonic transducers impacted by these types of defects are operational, they are defective in that the signal received is not an accurate signal. Therefore, such transducers are considered defective transducers. Also of interest to note is that ultrasonic transducer defects may develop over the course of normal usage of the sensor, for example due to thermal shocks or mechanical shocks that may lead to stresses, fractures, or local delaminations. These kinds of defects are especially hard to handle as there is no a priori knowledge about when/where they will occur. Embodiments described herein provide dynamic methods for correcting for defective or degraded ultrasonic transducers can adapt and handle issues as they develop.

Embodiments described herein provide a multiple step approach for handling defective or degraded ultrasonic transducers. FIG. 10 illustrates a flow diagram 1000 of an example method for detection and correction for defective or degraded ultrasonic transducers of an ultrasonic fingerprint sensor, according to embodiments.

In one embodiment, as illustrated in optional step 1010, the system (e.g., ultrasonic fingerprint sensor or electronic device including an ultrasonic fingerprint sensor) monitors for a self-test condition, where the system monitors for any events that may lead to defective or degraded ultrasonic transducers. For example, shock events can be monitored using internal sensors, such as a motion sensor monitoring for mechanical shock events (e.g., the electronic device including the fingerprint sensor is dropped) and/or a temperature sensor for thermal shock events (e.g., temperature extremes likely to impact fingerprint sensor hardware). In one embodiment, images are captured during operation of the fingerprint sensor and compared to a stored image for determining whether pixel values are indicative of defective or degraded ultrasonic transducers. If such an event occurs, the fingerprint sensor may be notified that a self-test for determining whether there are any defective or degraded ultrasonic transducers should be initiated. In other embodiments, a self-test is performed on a regular basis (e.g., periodically, on device start up).

In accordance with various embodiments, at procedure 1020, a defective or degraded ultrasonic transducer detection process is performed. In further embodiments, at procedure 1030, corrective action is taken to handle defective or degraded ultrasonic transducers. If now defective or degraded ultrasonic transducers were present before, the correction may be initiated, or if defective or degraded ultrasonic transducers were already present, the correction process may be updated.

In some embodiments, a self-test condition is detected for initiating a self-test of the ultrasonic transducers. It should be appreciated that the self-test condition may be scheduled periodically or performed in response to detection of a thermal or mechanical shock event, or detected by performing image analysis, etc.

Figure 11:
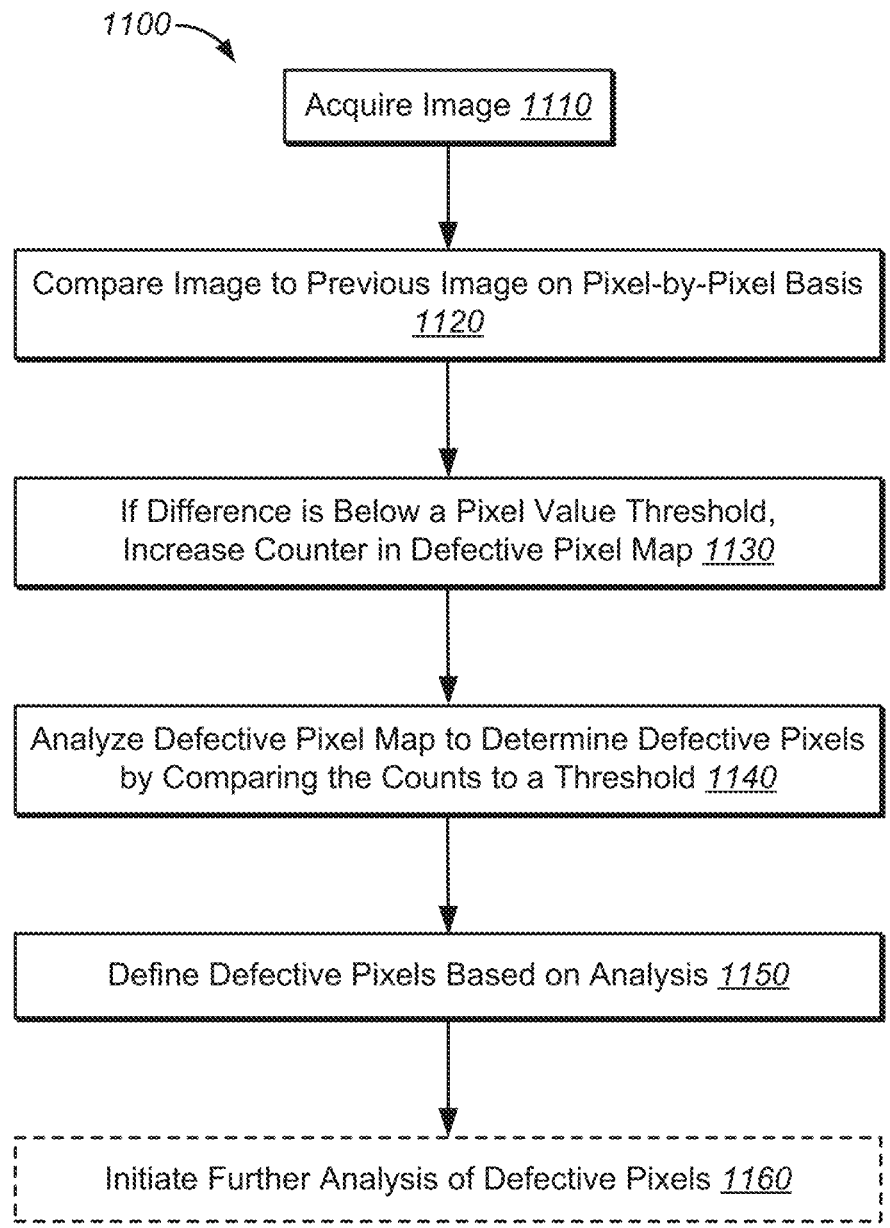
FIG. 11 illustrates a flow diagram of an example method for detection of a defective pixel of an image generated at an ultrasonic fingerprint sensor, according to embodiments.

FIG. 11 illustrates a flow diagram 1100 of an example method for detection of a defective pixel of an image generated at an ultrasonic fingerprint sensor, according to embodiments. In this method, detection of the defective pixels is done from images acquired from the sensor during normal operation, such as enrollment and verification images. The images from the sensor are monitored over time to see if some pixels always give a constant response or their behavior deviates from the neighboring pixels.

At procedure 1110 of flow diagram 1100, an image is captured using the ultrasonic sensing device. For example, the last image (e.g., most recent image) used for authentication from the sensor is stored. For example, the image is stored in a buffer of or accessible to the ultrasonic sensor.

At procedure 1120, the image is compared to a stored image captured using the ultrasonic sensor. In one embodiment, the stored image is captured at initialization of the ultrasonic sensor. In another embodiment, the stored image is a previous image captured at the ultrasonic sensor. In one embodiment, the comparison is performed and a defect accumulation map is maintained. The defect accumulation map may be initialized to all zero values. Whenever a new image is obtained for authentication, the current image is compared to a previous image. A difference in pixel value for pixels of the same location of the two images is determined.

At procedure 1130, it is determined whether a difference in pixel value is below a pixel value threshold. For instance, if the difference in pixel value is low, it may be indicative of a defective or degraded ultrasonic transducer having contributed to the pixel value, as a constant output of an ultrasonic transducer may be indicative of a defective or degraded ultrasonic transducer. For all pixels that have low differences between the current and the previous images, the corresponding pixel is identified as a candidate defective pixel and the pixel location in the defect accumulation map is incremented. However, if the difference is not low, the counter would not be incremented, as this is indicative of a properly functioning ultrasonic transducer. The difference may be compared to a pixel value threshold, where the pixel value threshold may be based on the overall signal quality, expected noise in the pixels, the typical finger prints of the user, or any other factor that may influence the difference. This results in pixels with real defects accumulating larger values over time. For pixels that are behaving normally, the corresponding values in the defect accumulation map would remain low as it is a low probability event that the same exact area of the finger is presented to the sensor repeatedly over a long time and the response from the pixel is not varying over time.

At procedure 1140, the defect accumulation map is analyzed at any point in time to find the defective pixels. At procedure 1150, defective pixels are defined based on the analysis. For example, in one embodiment, a candidate defective pixel threshold of defect accumulation map is compared to the counter for each pixel location, such that all pixels with values over the candidate defective pixel threshold are declared as defective pixels. The defect accumulation map could then be reset and the process started again to monitor further deterioration in the pixels.

At procedure 1160, in one embodiment, further analysis of the defective pixels is initiated. In one embodiment, a self-test condition is detected and a hardware analysis of defective or degraded ultrasonic transducers is initiated.

In various embodiments, the ultrasonic fingerprint sensor operates in a mode where groups of ultrasonic transducers operate collectively to create focused ultrasonic beams for capturing a pixel (e.g., more than one ultrasonic transducer is used for capturing one pixel), as described above in accordance with FIGS. 5-8. In addition to using a plurality of transducers for ultrasonic signal emission, e.g. subsets of ultrasonic transducers in a two-dimensional array of ultrasonic transducers, detection of the reflection ultrasonic waves may also be performed using a plurality of transducers, such as e.g. a 3×3 array of transducers/pixels during normal operation (e.g., image capture). Although the use of a plurality of transducers in the transmission and receiving of the ultrasound signal is beneficial for the image generation, these transmission patterns (Tx) and receive patterns (Rx) may interfere with the dead pixel detection because the measured signals do not reflect a single transducer/pixel.

Therefore, in some embodiments, the ultrasonic fingerprint sensor enters a self-test mode where it will capture an image specifically looking for defective or degraded ultrasonic transducers, where at least one of the transmission pattern and receiving pattern is adapted. In one embodiment, defective or degraded ultrasonic sensor detection, the ultrasonic fingerprint sensor uses a 1×1 transmission pattern and a 1×1 receive pattern. In one embodiment, the same ultrasonic transducer performs the signal transmission and the signal receive operations. Ultrasonic transducers with a low signal or no signal (e.g., below a signal threshold) are identified as defective or degraded ultrasonic transducers. Ultrasonic transducers with a very high signal (above expected limits) might also be identified as defective or degraded ultrasonic transducers.

In another embodiment, adjacent ultrasonic transducers perform the signal transmission and the signal receive operations, where one ultrasonic transducer performs the signal transmission operation and an adjacent ultrasonic transducer performs the signal receive operation. In the present embodiment, a scan of the entire fingerprint sensors using pairs of adjacent ultrasonic transducers is performed, where each ultrasonic transducer performs at least one transmit operation and one receive operation and is paired with different adjacent ultrasonic transducers for performing the different operations. A low signal or no signal received at the receiving ultrasonic transducer indicates that one ultrasonic transducer of the pair of ultrasonic transducers is defective, but not which one. A second comparison is performed, analyzing both the transmit and receive operations performed by each ultrasonic transducer. An ultrasonic transducer is identified as defective or degraded if both pairs of adjacent ultrasonic transducers in which it was included receive a low signal or no signal.

It should be appreciated that the self-test mode of operation to facilitate defective ultrasonic transducer detection maybe initiated on a regular basis or upon detection of events that may lead to dead pixels (over time). This self-test mode may be combined with the image analysis based method discussed above.

Figure 12A:
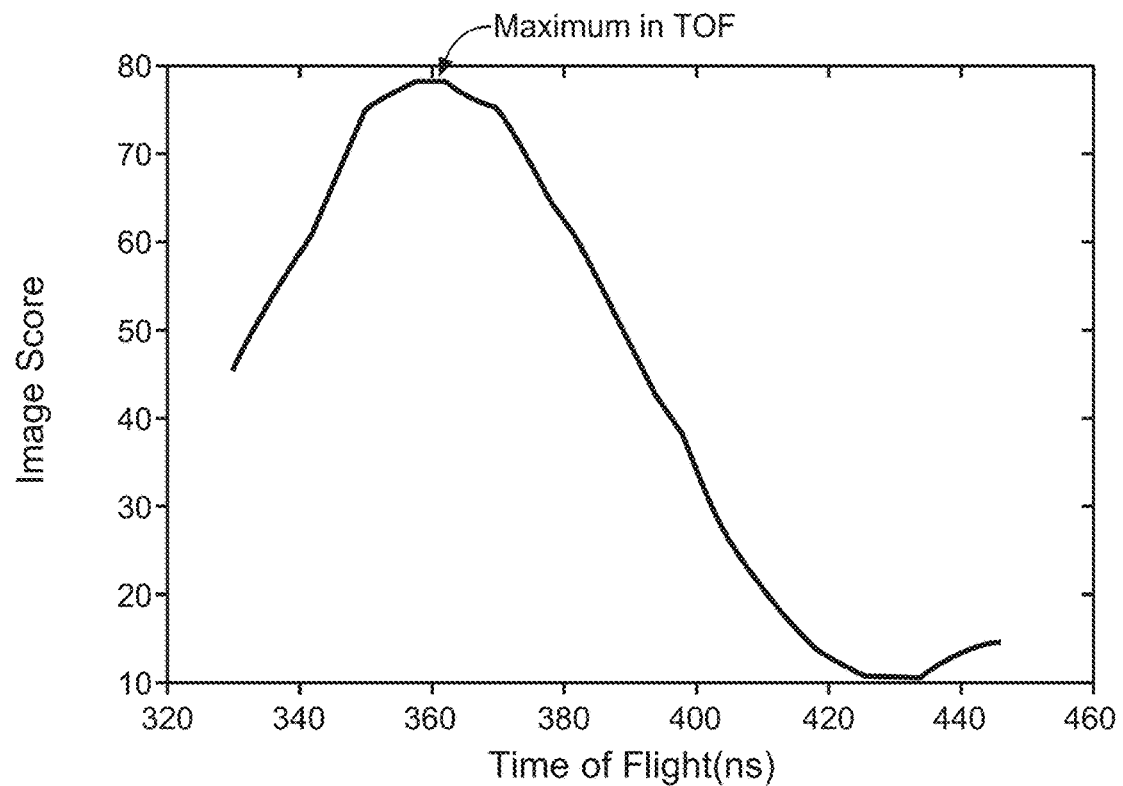
FIG. 12A shows an example time-of-flight (ToF) scan for a selected ultrasonic transducer, according to an embodiment.
Figure 12B:
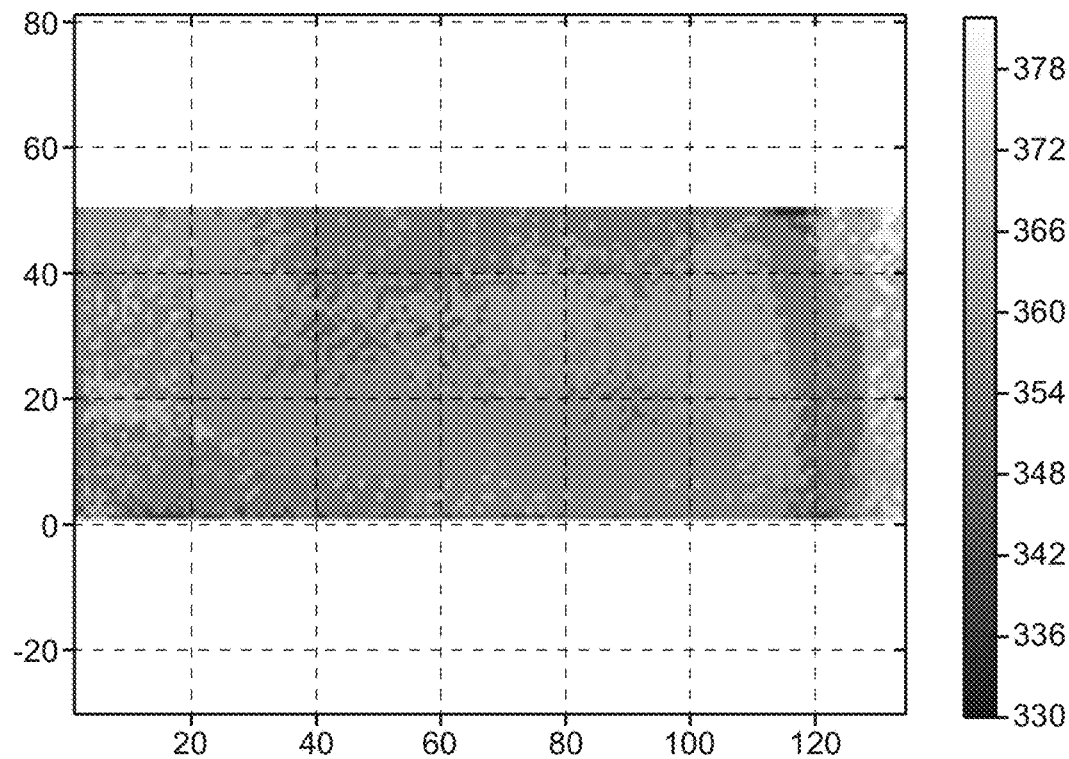
FIG. 12B illustrates an example ToF map for an ultrasonic sensor, according to an embodiment.

In another embodiment, the fingerprint sensor performs a self-calibrate intermittently where the characteristics of each ultrasonic transducer are measured. For ultrasonic sensors, the time-of-flight (ToF) is an important parameter that determines when in time the signal is acquired once the excitation/transmission pulse is sent. FIG. 12A illustrates an example ToF scan for a selected ultrasonic transducer, showing the reflected signal intensity as a function of the ToF. The maximum in the ToF for each ultrasonic transducer may be determined and plotted in a ToF map, as shown in FIG. 12B. It is expected that the ToF parameter will be similar for all the ultrasonic transducers. If an ultrasonic transducer or a group of ultrasonic transducers are defective, the ToF may be significantly different from the rest and this could be detected from a ToF map that stores the ToF parameter for each ultrasonic transducer. For example, if there are local delaminations/air bubbles/impurities in the stack, the ToF for those regions would be very different.

FIG. 12C illustrates an example image with no finger present, showing defective pixels corresponding to defective ultrasonic transducers in the top center of the sensor. The darker color of the pixels in the map represents a lack of signal because of a shorter ToF due to a reflection caused by delamination of one of the layers in the sensor stack. The shorter ToF is outside the standard ToF window for collecting signals from a finger, and therefore no signal is acquired. In this mode, for each ultrasonic transducer the reflected signal intensity is measured as a function of the ToF, and then a characteristic of the measure distribution is used to detect the dead or malfunctioning ultrasonic transducer. For example, the maximum of the ToF distribution may be used (as shown in FIG. 12A). Alternatively, the width of the distribution, or any other characteristic may be used. Multiple transducers that are defective and in close proximity may be grouped together, to define groups, set, and/or regions of defective pixels. Based on the ToF it can be determined which layer has the delamination defects. In embodiments with many different layers, e.g., a finger print sensor integrated in an OLED display, it may be determined where problems due to delamination occur. This information may be communicated, e.g., to the manufacturer of the sensor or device.

The self-test routines described above could run in conjunction with finger detection modules that would verify that there is nothing on the sensor when the test is run. The ultrasonic sensor could try to run this test on a predetermined schedule such as every day or every week. It might also be possible to adapt the frequency of the sensor self-test based on the number of defects that are being detected. For example, if more and more ultrasonic transducers are being found as defective, the frequency of the self-test scans could be increased.

Defective or degraded ultrasonic transducers have an impact on several aspects of the ultrasonic sensor performance. For instance, in finger detect mode, the ultrasonic sensor might be using only a small number of pixels. The finger detection operation may use different levels. For example, in a first level (e.g., FDMA) only a few ultrasonic transducers are activated to so if an object is interacting with the ultrasonic sensor. If this is the case, in a next level (e.g., FDMB) more ultrasonic transducers may be activated. For example, where lines of pixels or patches of pixels are captured (e.g., FDMC), correspondingly larger amounts of ultrasonic transducers may be activated, to verify if the object has characteristics similar to a finger print. This method helps keep power consumption low, because each of the successive stages uses more pixels than the prior stage and is only activated if the previous stage shows positive results. In one implementation, a first stage uses, e.g., 50 pixels, a second stage uses, e.g., 500 pixels, and a third stage uses, e.g., 2000 pixels. If some of the ultrasonic transducers being used are defective, it will have a significant impact on the final system performance and the different levels of finger detection might be affected to different extents by the same set of dead ultrasonic transducers. Moreover, ultrasonic transducers being used in this process may also be activated more than other ultrasonic transducers, and therefore may have a higher likelihood of showing issues during the lifetime of the ultrasonic sensor. To monitor this process, the defective ultrasonic transducer testing may not be uniform, but may survey ultrasonic transducers used in the finger detection process more thoroughly, e.g., more frequently.

In one embodiment, after identification of defective ultrasonic transducers, the ultrasonic fingerprint sensor operates to selected alternate ultrasonic transducers or avoids defective ultrasonic transducers in pixel capture operations. For instance, once defective ultrasonic transducer identification flags that a particular ultrasonic transducer is defective, properly functioning ultrasonic transducers in its neighborhood, e.g., adjacent or nearby, could be chosen to replace the defective ultrasonic transducer. For example, in finger detect operation stage that use pixels along lines, alternate lines that have fewer defective ultrasonic transducers can be chosen.

For authentication purposes, the defective ultrasonic transducers would cause patterns that are seemingly constant between images and could confuse the image matcher used for fingerprint authentication and user identification. One method to mitigate this is to use the defective ultrasonic transducer map from the detection and to interpolate the image information for these pixels from neighboring pixels before sending the image to the matcher. Alternatively, the matcher may have access to the defective ultrasonic transducer map, or a register of the defective pixels may be communicated to the matcher, and the matcher may compensate for the effects of the defective transducers on the fingerprint image before performing the authentication. In other embodiments, the different pixels may be given different weights in any process or calculation such as the user authentication. The weight of the pixels may depend on related defective transducers. If more of the transducers contributing to the pixel acquisition are defective, the weight of the pixels may be e.g. decreased due to its decreased reliability. The weight of the pixel may also depend on its location, where pixels closer to the center of the image are more important, and thus the influence of a defective transducer close the center of the sensor may be more significant. Groups/regions of defective transducers may also be given a weight, where the weight depends on the size of the group or region. In one embodiment, performance data of one or more ultrasonic transducers, or all ultrasonic transducers (e.g., the complete sensor) may be made available or communicated to the matcher. The performance data of the transducers may indicate whether or not a transducer is defective, whether the transducer is otherwise underperforming, the confidence in the transducer data, or any other performance indicators. The performance data may also be communicated to other parties, e.g., the manufacturer or the sensor or of the device.

In another defective ultrasonic transducer handling scheme, it would be possible to compensate for a defective ultrasonic transducer by changing calibration parameters. In some embodiments, the ultrasonic sensor has a set of gain and offset values that are applied to each ultrasonic transducer to accommodate for variations in the signal chain inherent in the design/manufacturing process. When a 3×3 receive pattern is used as described previously, the output value for a particular ultrasonic transducer is the average of the responses obtained in a 3×3 region. If one or more of the ultrasonic transducer in this region become non-responsive, the contribution to the final signal reduces by a factor. For example, if one ultrasonic transducer in the 3×3 region is defective, the resulting signal would be $8/9^{th}$ of what it should have been. In this case, the gain for each operational ultrasonic transducer can be increased by a factor such as $9/8$ to compensate for the resulting signal loss. In this way, the system can account for defective ultrasonic transducers as they develop in the field with minimal overhead as changing the calibration value will result in an output image that is already compensated. This may decrease the effect of the ultrasonic transducer averaging on the noise, and a threshold may be set if too many ultrasonic transducers in the receive pattern are dead or the signal to noise ratio (SNR) becomes too small. If the gain compensation does no longer give satisfactory results because of too many defective ultrasonic transducers, the system may switch to alternative methods, such as the image based interpolation described above.

In another defective ultrasonic transducer handling scheme, neighboring ultrasonic transducers are used for recovering information lost by defective ultrasonic transducer. For example, in some ultrasonic sensors, the signal that is sent out is adjusted to focus on a particular spot on the sensor stack. This is accomplished by sending sound pulses from multiple ultrasonic transducers at varying delays to performed beam forming, as discussed in relation to FIG. 5. In various embodiments, the beam forming pattern is changed to help recover information about defective ultrasonic transducers from surrounding ultrasonic transducers. As mentioned previously, for each pixel in the output image, a signal is received on multiple ultrasonic transducers (defined by a receive pattern). It would be possible to accurately recover the actual signal at a defective ultrasonic transducer by signal processing the received signals from surrounding regions. In order words, during both the signal transmission process and the signal receiving process the beam forming may be adapted to correct/compensate for defective ultrasonic transducers. For example, the phase delay patterns, as shown in FIGS. 5, 7A, and 7B, may be adapted to correct for the effect of a defective ultrasonic transducers on the beamforming by adjusted the phase of the surrounding ultrasonic transducers. Moreover, the beam can be steered around patches of ultrasonic transducers where too many defective ultrasonic transducers are present to be corrected through the phase delay pattern (see, e.g., focused beam 859 of FIG. 8).

Figure 13:
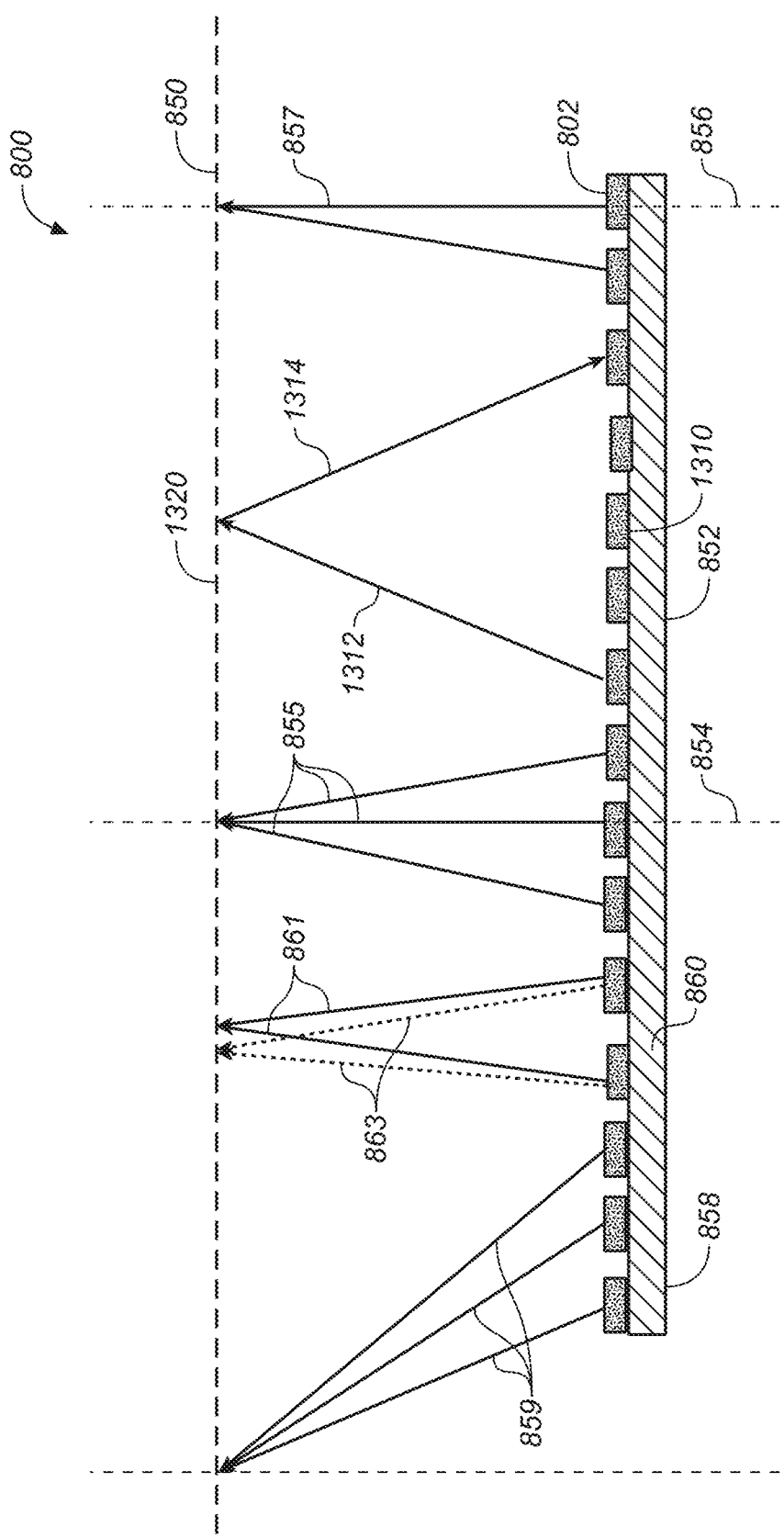
FIG. 13 illustrates the example ultrasonic transducer system of FIG. 8 including an identified defective ultrasonic transducer, according to an embodiment.

In some embodiments, the beam forming and beam steering may be adapted so that the number of defective ultrasonic transducers in the receive pattern are minimized. Geometry consideration and characteristics of the ultrasonic wave propagation and reflection may be used to control the propagation of the waves to avoid the dead pixels. FIG. 13 illustrates the example ultrasonic transducer system 800 of FIG. 8, where defective ultrasonic transducer 1310 has been identified. FIG. 13 illustrates an example of using beam forming and steering to handle and correct for defective ultrasonic transducer 1310. The arrows 1312 and 1314 represent the path of the acoustic waves to image a pixel at position 1320 on line 850, to account for defective ultrasonic transducer 1310 underlying position 1320. The adapted control of the transducers may be based on geometric consideration, but may also be determined based on a process where various configurations of transducers control are tested and compared to expected results.

It should be appreciated that adaption of the beamforming to correct for the defective ultrasonic transducers may require more time, and processing and power resources than operation with correcting for defective ultrasonic transducers. Therefore, this process may be applied selectively. For example, the correction for defective ultrasonic transducers may only be applied upon detection of a certain amount of defective ultrasonic transducers, making user authentication otherwise difficult. The type of application for which authentication is required may also determine if all ultrasonic transducer defects need to be corrected for. For example, for high level banking application, the best possible fingerprint image must be provided, and this requires correcting for the defective ultrasonic transducers. Therefore, operation of the ultrasonic transducers may be performed according to different modes that require a different level of precision, accuracy, and/or confidence. In the different modes, the correction for the defective ultrasonic transducers may be performed differently. For example, in a normal mode, no correction for the defective ultrasonic transducers may be performed, while in another 'high-performance' mode, corrective action to compensate for the defective ultrasonic transducers may be performed, at a higher power and computational cost. The mode selection may depend on the application or class of application requesting the sensor operation.

FIGS. 14A through 18 illustrate flow diagrams of example methods for operating a fingerprint sensor comprised of ultrasonic transducers, according to various embodiments. Procedures of these methods will be described with reference to elements and/or components of various figures described herein. It is appreciated that in some embodiments, the procedures may be performed in a different order than described, that some of the described procedures may not be performed, and/or that one or more additional procedures to those described may be performed. The flow diagrams include some procedures that, in various embodiments, are carried out by one or more processors (e.g., a host processor or a sensor processor) under the control of computer-readable and computer-executable instructions that are stored on non-transitory computer-readable storage media. It is further appreciated that one or more procedures described in the flow diagrams may be implemented in hardware, or a combination of hardware with firmware and/or software.

Figure 14A:
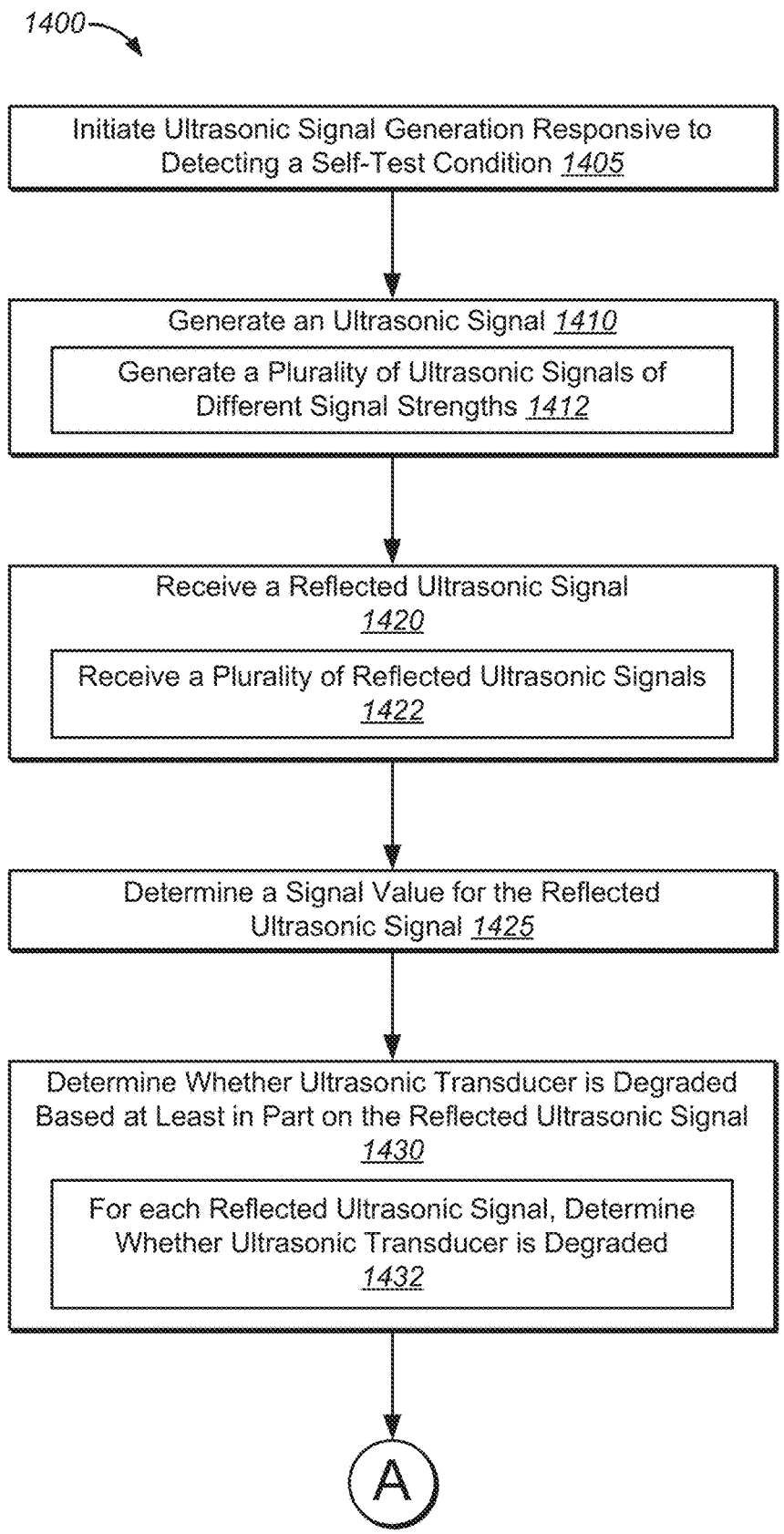
FIGS. 14A through 18 illustrate flow diagrams of example methods for operating a fingerprint sensor comprised of ultrasonic transducers, according to various embodiments.
Figure 14B:
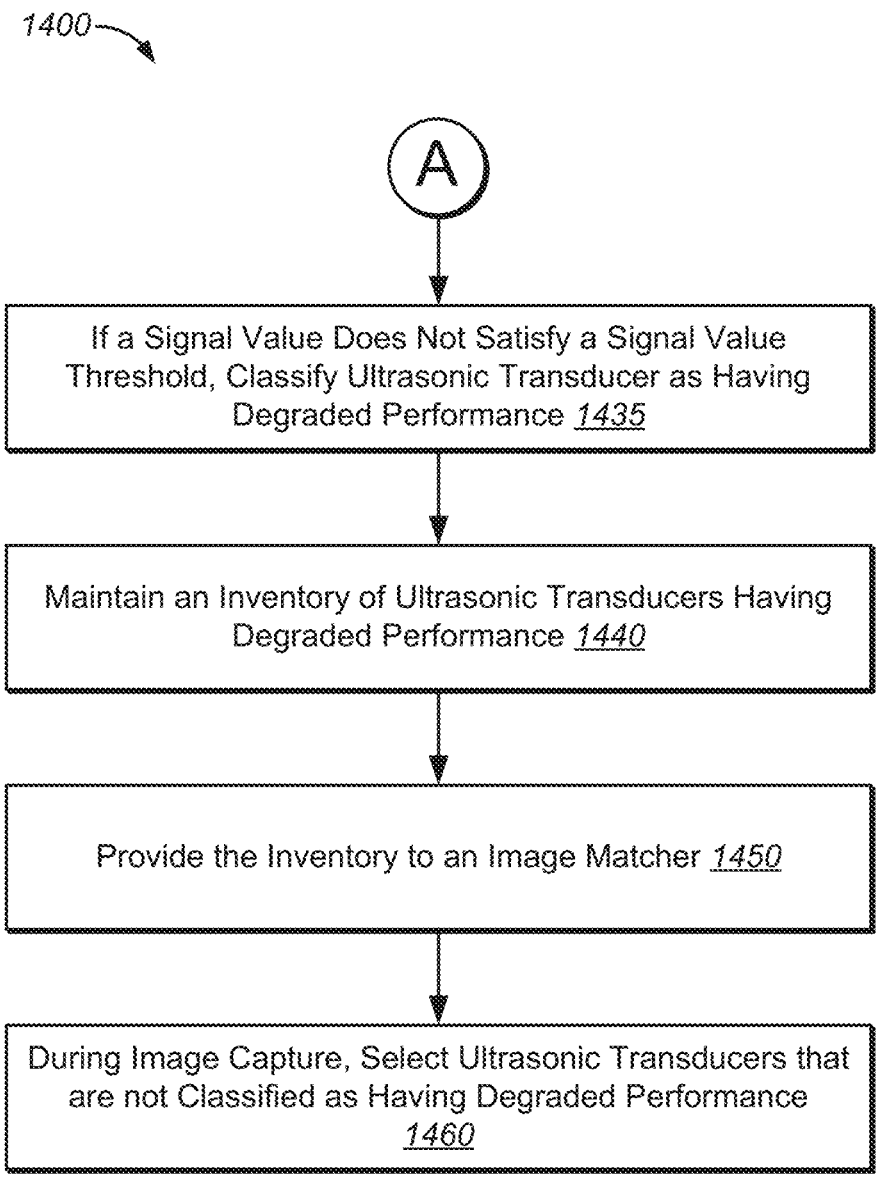

With reference to FIGS. 14A and 14B, flow diagram 1400 of an example method for detection of defective ultrasonic transducers in an in ultrasonic sensing device, according to various embodiments, is shown. At procedure 1405 of FIG. 14A, in accordance with one embodiment, ultrasonic signal generation (e.g., procedure 1410) is initiated in response to detecting a self-test condition. For example, the ultrasonic sensing device monitors for a self-test condition such as shock events, image analysis and comparison, etc.

At procedure 1410, an ultrasonic signal is generated at an ultrasonic sensing device including a plurality of ultrasonic transducers. In some embodiments, the ultrasonic signal is generated at one ultrasonic transducer of the plurality of ultrasonic transducers. In another embodiment, the ultrasonic signal is generated using a beam forming pattern of ultrasonic transducers of the plurality of ultrasonic transducers. In one embodiment, as shown at procedure 1412, a plurality of ultrasonic signals of different signal strengths is generated. For example, a weaker signal may not provide enough differentiation to generate an accurate pixel, but at higher signal strengths, the ultrasonic transducer may be capable of generating an accurate pixel. By using varying signal strengths, it can be determined whether an ultrasonic transducer may be degraded at particular signal strengths, allowing for appropriate correction.

At procedure 1420, a reflected ultrasonic signal corresponding to the ultrasonic signal generated at at least one ultrasonic transducer of the plurality of ultrasonic transducers is received. In one embodiment, as shown at procedure 1422, a plurality of reflected ultrasonic signals is received corresponding to the plurality of ultrasonic signals of different signal strengths. In one embodiment, as shown at procedure 1425, a signal value for the reflected ultrasonic signal or signals is received.

At procedure 1430, it is determined whether performance of at least one ultrasonic transducer is degraded based at least in part on the reflected ultrasonic signal. In one embodiment, as shown at procedure 1432, where there are a plurality of reflected ultrasonic signals, it is determined whether the ultrasonic transducer is degraded for each reflected ultrasonic signal.

Figure 15:
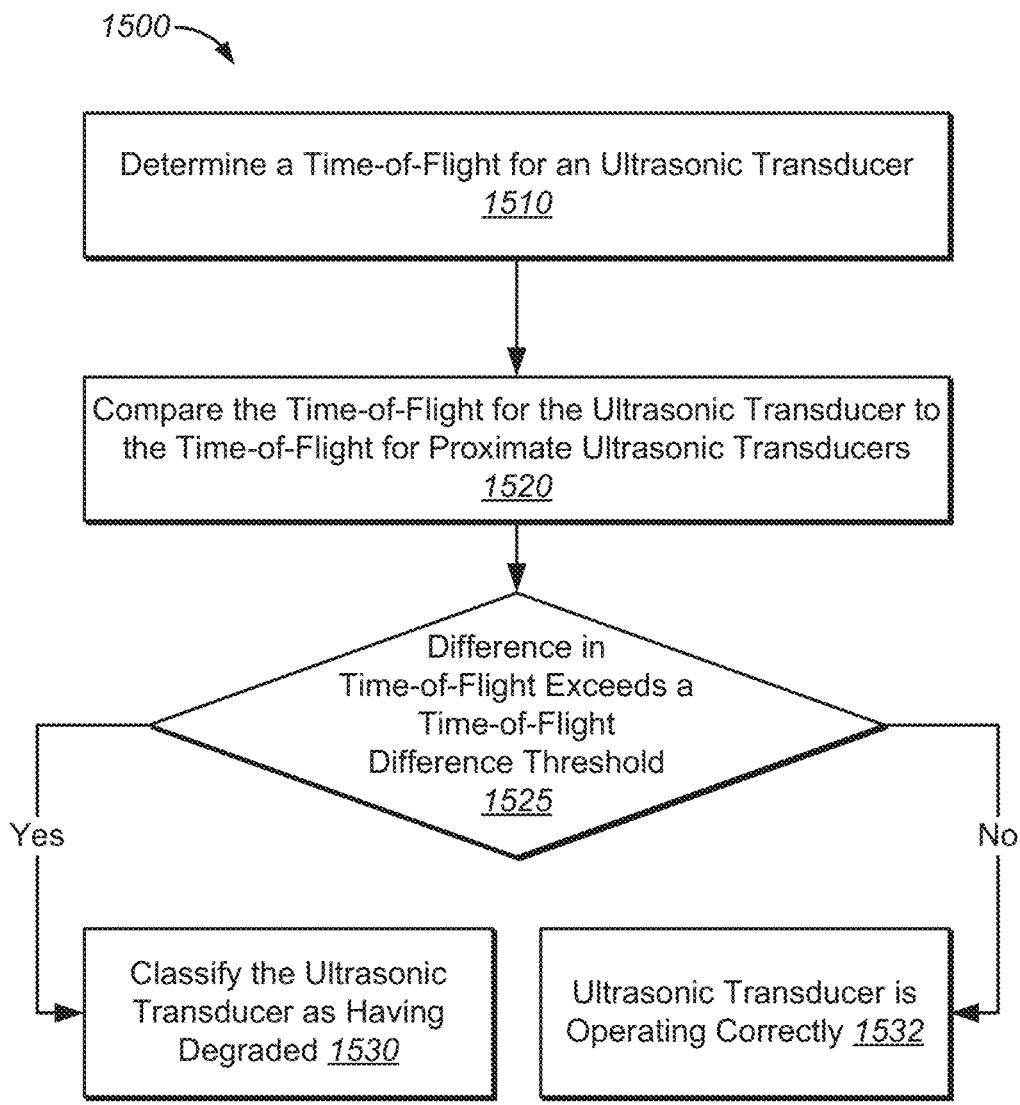

In one embodiment, procedure 1430 is performed according to flow diagram 1500 of FIG. 15. With reference to FIG. 15, flow diagram 1500 of an example method for using time-of-flight (ToF) to determine whether performance of an ultrasonic transducer has degraded, according to an embodiment. At procedure 1510, a ToF is determined for a signal transmitted by an ultrasonic transducer. At procedure 1520, the ToF determined at procedure 1510 is compared to the ToF for proximate ultrasonic transducers (e.g., adjacent ultrasonic transducers or nearby ultrasonic transducers), or any other reference ultrasonic transducers or reference ToF value. In one embodiment, a difference in the ToF determined at procedure 1510 and the ToF for proximate ultrasonic transducers is determined.

At procedures 1525, it is determined whether the difference in ToF exceeds a ToF difference threshold. Where the difference in ToF exceeds the ToF difference threshold, as illustrated at procedure 1530, the ultrasonic transducer is classified as having degraded. Where the difference in ToF does not exceed the ToF difference threshold, as illustrated at procedure 1532, the ultrasonic transducer is operating correctly.

With reference to FIG. 14B, in accordance with an embodiment, as shown at procedure 1435, if a signal value (e.g., as received at procedure 1425) is does not satisfy a signal value threshold (e.g., is above or below the signal value threshold), the ultrasonic transducer is classified as having degraded performance. It should be appreciated that many different types of corrective action can also be initiated or performed, e.g., interpolation of pixel values, adjustment of gain calibration, adjust beam forming patterns, etc.) in response to detecting a signal value not satisfying the signal value threshold. In one embodiment, the signal value threshold is an absolute value of the ultrasonic sensing device, or region of the ultrasonic sensing device. In one embodiment, the signal value threshold is a relative value with respect to neighboring and/or proximate ultrasonic transducers.

In one embodiment, as shown at procedure 1440, an inventory of ultrasonic transducers having degraded performance is maintained. In one embodiment, the inventory is a map of the plurality of ultrasonic transducers including indicators of locations of degraded or defective ultrasonic transducers. In another embodiment, the inventory comprises a list of degraded or defective ultrasonic transducers. In some embodiments, a weight can be applied to the defective/degraded ultrasonic transducers. For example, groups of proximate defective ultrasonic transducers may be assigned a higher weight than defective ultrasonic transducers that are not proximate other ultrasonic transducers. In other examples, defective ultrasonic transducers near an edge of the ultrasonic fingerprint sensor may be assigned a lower weight than defective ultrasonic transducers not near an edge.

In one embodiment, as shown at procedure 1450, the inventory of ultrasonic transducers having degraded performance is provided to an image matcher for use in performing fingerprint authentication.

In one embodiment, as shown at procedure 1460, during image capture, the ultrasonic sensing device intentionally does not select ultrasonic transducers that are classified as having degraded performance.

Figure 16A:
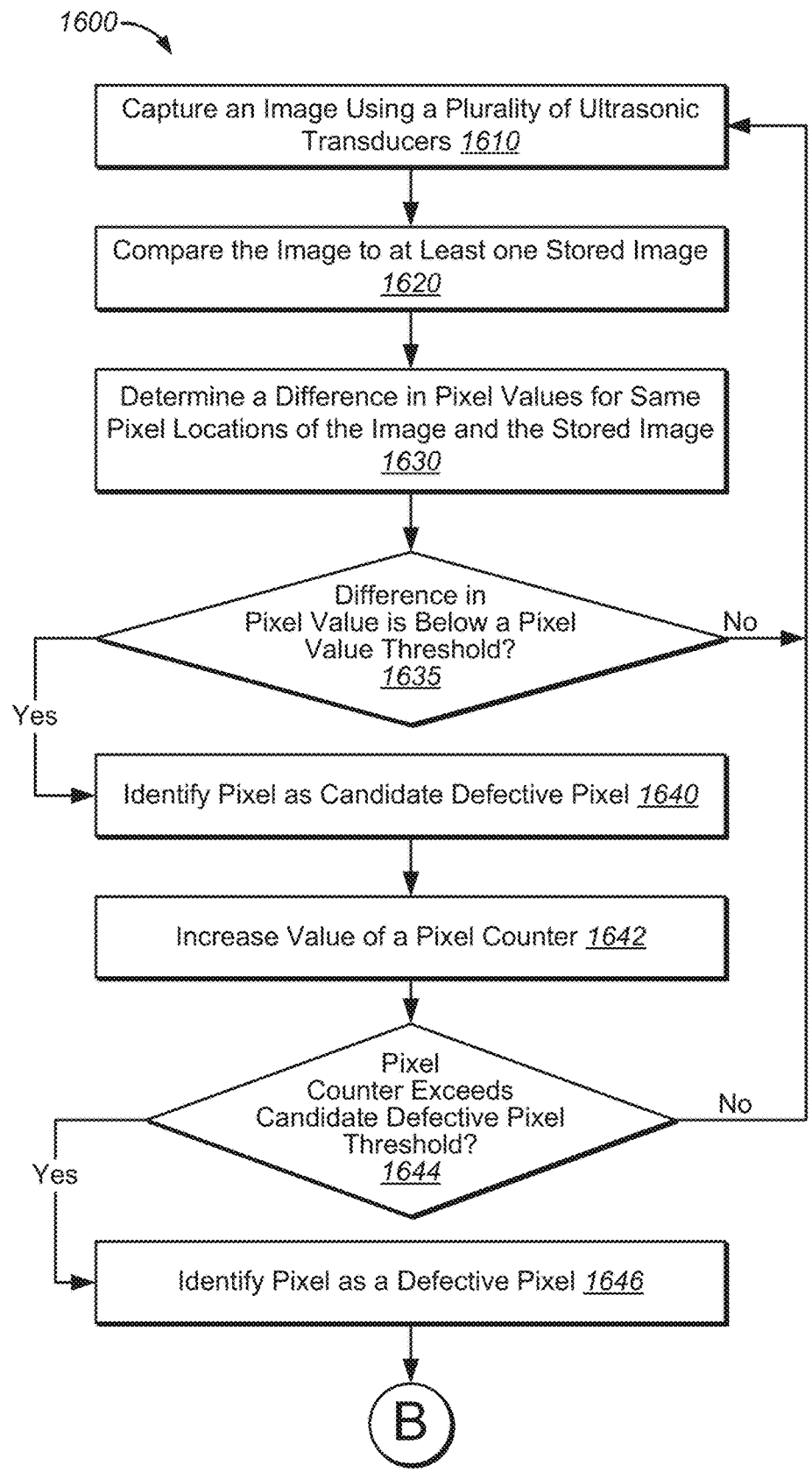
Figure 16B:
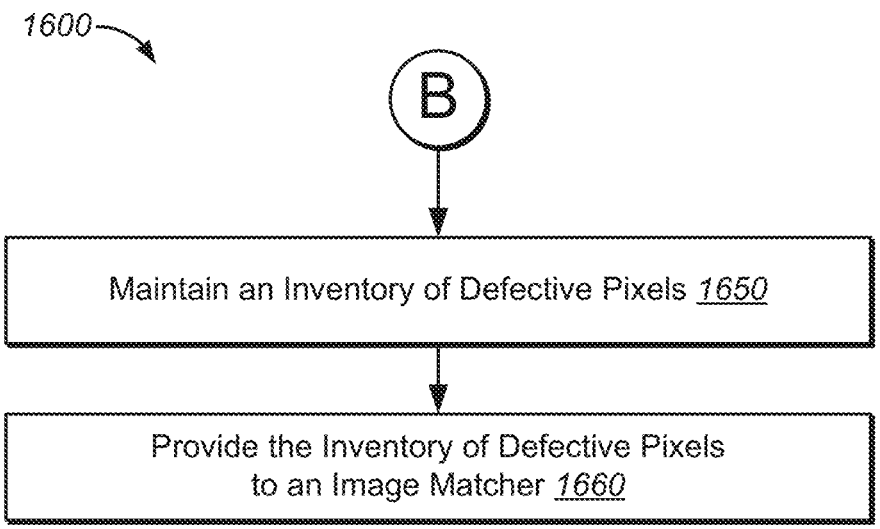
Figure 16C:
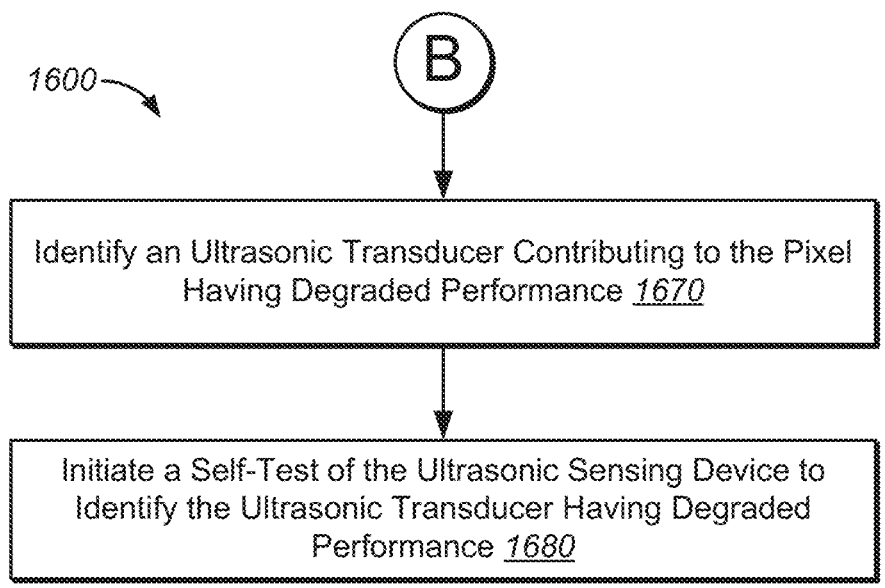

With reference to FIGS. 16A through 16C, flow diagram 1600 of an example method for detection of defective pixels of an image captured by an ultrasonic sensing device, according to various embodiments, is shown. At procedure 1610 of FIG. 16A, in accordance with one embodiment, an image is captured using the ultrasonic sensing device, wherein the ultrasonic sensing device includes a plurality of ultrasonic transducers.

At procedure 1620, the image is compared to at least one stored image captured using the plurality of ultrasonic transducers of the ultrasonic sensing device.

At procedure 1630, a difference in pixel value between a pixel having a same location in the image and at least one stored image is determined. At procedure 1635, it is determined whether the difference in pixel value is below a pixel value threshold. Provided the difference in pixel value is below the pixel value threshold, as illustrated at procedure 1640, the corresponding pixel is identified as a candidate defective pixel. Provided the difference in pixel value is not below the pixel value threshold, flow diagram 1600 returns to procedure 1610 for further processing (e.g., after a predetermined time has elapsed or a self-test condition is detected).

In one embodiment, as shown at procedure 1642, the value of a pixel counter for the corresponding pixel is increased. At procedure 1644, it is determined whether the pixel counter exceeds a candidate defective pixel threshold. The candidate defective pixel threshold operates to protect against overly aggressive determinations of defective pixels, ensuring that a pixel is determined as a candidate defective pixel a number of times (e.g., 10 or 20 times) before the pixel is identified as defective. Provided the pixel counter exceeds a candidate defective pixel threshold, as illustrated at procedure 1646, the corresponding pixel is identified as a defective pixel. Provided the pixel counter does not exceed a candidate defective pixel threshold, flow diagram 1600 returns to procedure 1610 for further processing. It should be appreciated that many different types of corrective action can also be initiated or performed, e.g., interpolation of pixel values, adjustment of gain calibration, adjust beam forming patterns, etc.) in response to identifying a defective pixel.

With reference to FIG. 16B, in one embodiment, flow diagram 1600 proceeds to procedure 1650. At procedure 1650, an inventory of defective pixels is maintained. In one embodiment, the inventory is a pixel map indicating locations of defective pixels. In another embodiment, the inventory comprises a list of defective pixels. In one embodiment, as shown at procedure 1660, the inventory of defective pixels is provided to an image matcher for use in performing fingerprint authentication.

With reference to FIG. 16C, in one embodiment, flow diagram 1600 proceeds to procedure 1670. In one embodiment, as shown at procedure 1670, an ultrasonic transducer contributing to the defective pixel is identified. In one embodiment, as shown at procedure 1680, a self-test condition of the ultrasonic sensing device is initiated to identify the ultrasonic transducer having degraded performance. In accordance with some embodiments, the self-test is performed as described in accordance with FIGS. 14A and 14B.

Figure 17:
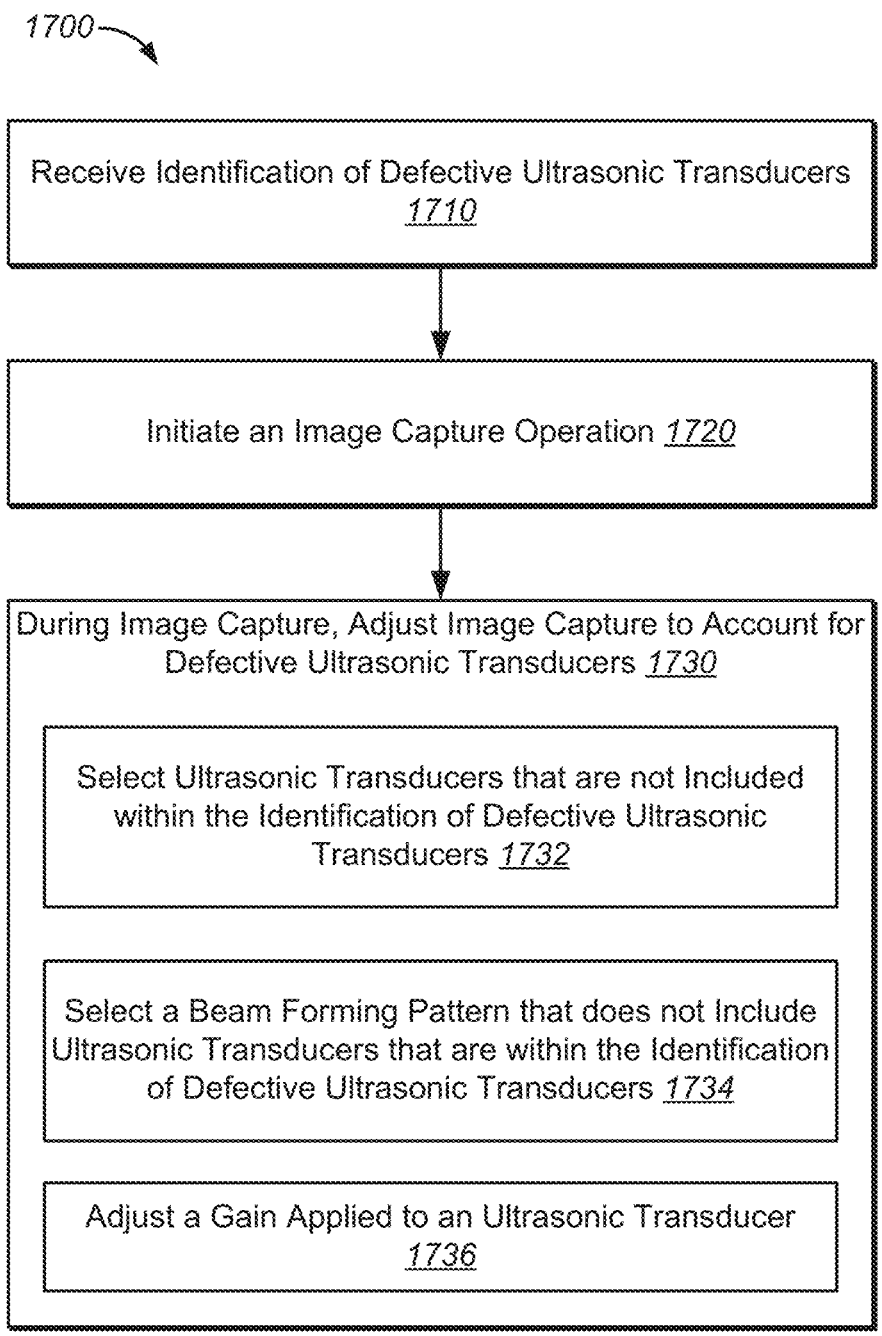

Upon identification of defective ultrasonic transducers, corrective or ameliorative action can be taken. FIG. 17 illustrates flow diagram 1700 of an example method for operating an ultrasonic sensing device comprising a plurality of ultrasonic transducers, according to an embodiment. At procedure 1710, an identification of defective ultrasonic transducers is received. At procedure 1720, an image capture operation is initiated by the plurality of ultrasonic transducers.

At procedure 1730, the image capture operation is adjusted during operation to account for the defective ultrasonic transducers. In one embodiment, as shown at procedure 1732, ultrasonic transducers of the plurality of ultrasonic transducers that are not comprised within the identification of defective ultrasonic transducers are selected to capture pixels of an image. In another embodiment, as shown at procedure 1734, a beam forming pattern comprising a plurality of ultrasonic transducers that does not comprise ultrasonic transducers within the identification of defective ultrasonic transducers is selected. In another embodiment, as shown at procedure 1736, a gain applied to at least one ultrasonic transducer of the plurality of ultrasonic transducers is adjusted.

Figure 18:
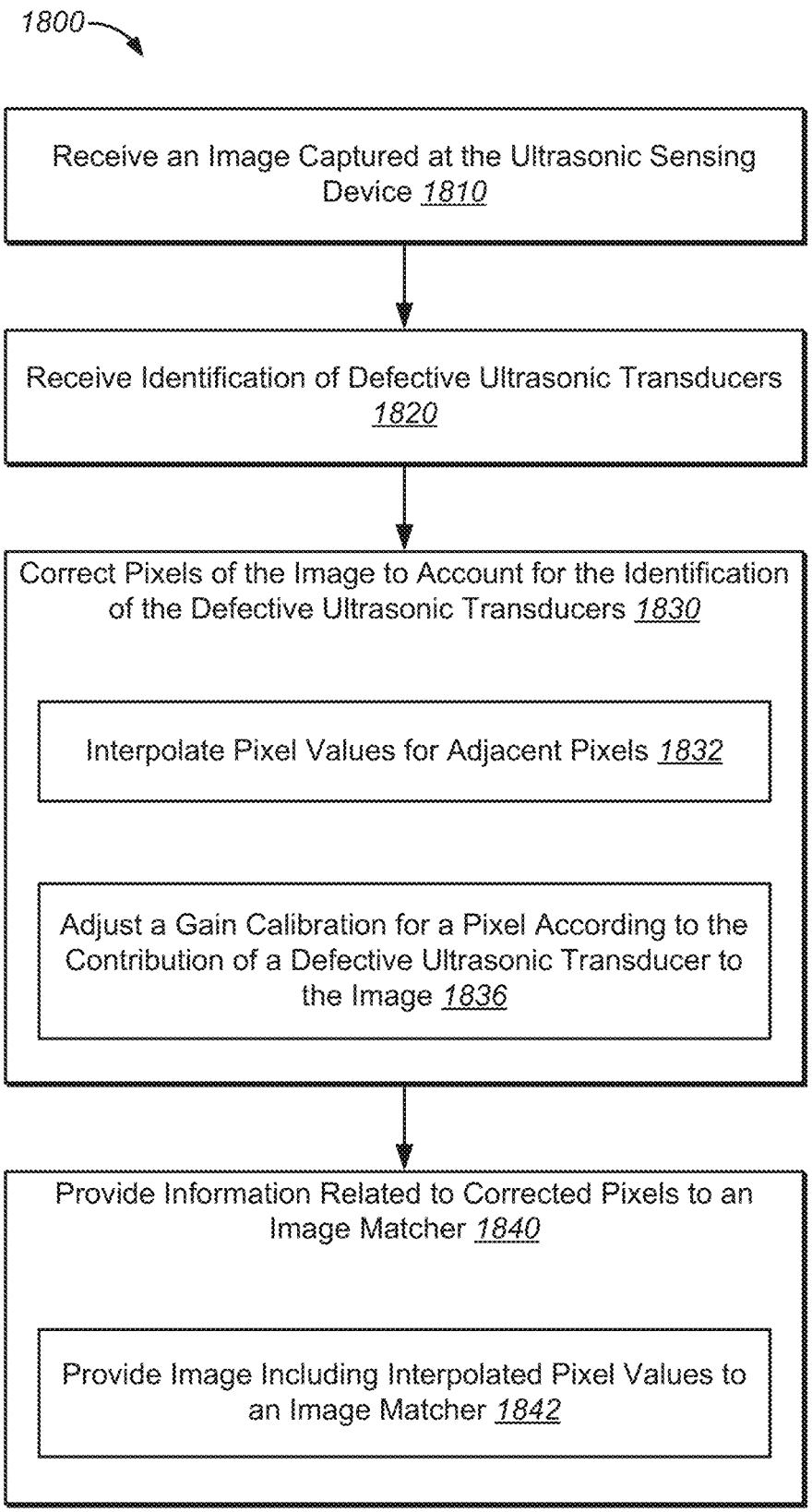

In accordance with some embodiments, an image can be corrected upon identification of the defective ultrasonic transducers. FIG. 18 illustrates flow diagram 1800 of an example method for correcting an image captured at an ultrasonic sensing device comprising a plurality of ultrasonic sensors, according to an embodiment. At procedure 1810, an image captured at the ultrasonic sensing device is received. At procedure 1820, an identification of defective ultrasonic transducers of the ultrasonic sensing device is received.

At procedure 1830, pixels of the image are corrected to account for the identification of defective ultrasonic transducers. In one embodiment, as shown at procedure 1832, pixel values for adjacent pixels are interpolated for pixels captured with at least one defective ultrasonic transducer. In another embodiment, as shown at procedure 1836, a gain calibration for at least one pixel is adjusted according to a contribution of at least one defective ultrasonic transducer to the image.

In one embodiment, as shown at procedure 1840, information related to the pixels of the image that were corrected is provided to an image matcher. In one embodiment, as shown at procedure 1842, subsequent interpolating pixel values for adjacent pixels for pixels captured with at least one defective ultrasonic transducer, the image comprising interpolated pixel values is provided to the image matcher.

What has been described above includes examples of the subject disclosure. It is, of course, not possible to describe every conceivable combination of components or methodologies for purposes of describing the subject matter, but it is to be appreciated that many further combinations and permutations of the subject disclosure are possible. Accordingly, the claimed subject matter is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter.

The aforementioned systems and components have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components. Any components described herein may also interact with one or more other components not specifically described herein.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Thus, the embodiments and examples set forth herein were presented in order to best explain various selected embodiments of the present invention and its particular application and to thereby enable those skilled in the art to make and use embodiments of the invention. However, those skilled in the art will recognize that the foregoing description and examples have been presented for the purposes of illustration and example only. The description as set forth is not intended to be exhaustive or to limit the embodiments of the invention to the precise form disclosed.

What is claimed is:

1. A method for detection of defective ultrasonic transducers in an ultrasonic sensing device, the method comprising:

generating an ultrasonic signal at an ultrasonic sensing device comprising a plurality of ultrasonic transducers;
receiving a reflected ultrasonic signal corresponding to the ultrasonic signal at at least one ultrasonic transducer of the plurality of ultrasonic transducers; and
determining whether performance of the at least one ultrasonic transducer is degraded based at least in part on the reflected ultrasonic signal, for the plurality of ultrasonic transducers:

determining a time-of-flight for the at least one ultrasonic transducer based at least on the ultrasonic signal and the reflected ultrasonic signal;
comparing the time-of-flight for the at least one ultrasonic transducer to the time-of-flight for proximate ultrasonic transducers; and
provided a difference between the time-of-flight for the at least one ultrasonic transducer and the time-of-flight for proximate ultrasonic transducers exceeds a time-of-flight difference threshold, classifying the at least one ultrasonic transducer as having degraded performance.

2. The method of claim 1, wherein the determining whether performance of the at least one ultrasonic transducer is degraded is also based at least in part on a reflected ultrasonic signal generated at at least one adjacent ultrasonic transducer of the plurality of ultrasonic transducers.

3. The method of claim 1, further comprising:
determining a signal value for the reflected ultrasonic signal; and
provided the signal value does not satisfy a signal value threshold, classifying the at least one ultrasonic transducer as having degraded performance.

4. The method of claim 1, wherein the generating the ultrasonic signal comprises:
generating a plurality of ultrasonic signals of different signal strengths; and
wherein the receiving a reflected ultrasonic signal corresponding to the ultrasonic signal comprises:
receiving a plurality of reflected ultrasonic signals corresponding to a plurality of ultrasonic signals.

5. The method of claim 4, further comprising:
for each reflected ultrasonic signal of the plurality of reflected ultrasonic signals, determining whether performance of the at least one ultrasonic transducer is degraded for a corresponding signal strength based at least in part on the reflected ultrasonic signal for the corresponding signal strength.

6. The method of claim 1, further comprising:
initiating the generating the ultrasonic signal responsive to detecting a self-test condition.

7. The method of claim 6, wherein the self-test condition comprises at least one of a thermal shock event or a mechanical shock event.

8. The method of claim 7, wherein the difference is used to determine a layer defect in the ultrasonic sensing device.

9. The method of claim 8, wherein the layer defect is a delamination defect.

10. The method of claim 6, further comprising:
capturing an image using the plurality of ultrasonic transducers of the ultrasonic sensing device;
comparing the image to at least one stored image captured using the plurality of ultrasonic transducers of the ultrasonic sensing device;
determining a difference in pixel value between a pixel having a same location in the image and the at least one stored image; and
provided the difference in the pixel value between the pixel having the same location in the image and the at least one stored image is below a pixel value threshold, detecting the self-test condition.

11. The method of claim 1, further comprising:
maintaining an inventory of ultrasonic transducers having degraded performance.

12. The method of claim 11, further comprising:
providing the inventory of ultrasonic transducers having degraded performance to an image matcher.

13. The method of claim 11, further comprising:
during image capture, selecting ultrasonic transducers of the plurality of ultrasonic transducers that are not determined as having degraded performance.

14. A method for detection of a defective pixel of an image captured by an ultrasonic sensing device, the method comprising:
capturing an image using the ultrasonic sensing device, wherein the ultrasonic sensing device comprises a plurality of ultrasonic transducers;
comparing the image to at least one stored image captured using the plurality of ultrasonic transducers of the ultrasonic sensing device;
determining a difference in pixel value between a pixel having a same location in the image and the at least one stored image; and
provided the difference in the pixel value between the pixel having the same location in the image and the at least one stored image is below a pixel value threshold, identifying the pixel as a candidate defective pixel.

15. The method of claim 14, further comprising:
increasing a value of a counter for the pixel in response to identification of the pixel as a candidate defective pixel; and
provided the counter exceeds a candidate defective pixel threshold, identifying the pixel as a defective pixel.

16. The method of claim 15, further comprising:
maintaining an inventory of defective pixels.

17. The method of claim 16, further comprising:
providing the inventory of defective pixels to an image matcher.

18. The method of claim 15, further comprising:
identifying an ultrasonic transducer contributing to the capturing of the pixel that has degraded performance.

19. The method of claim 18, wherein the identifying an ultrasonic transducer contributing to the capturing of the pixel that has degraded performance comprises:
initiating a self-test of the ultrasonic sensing device to identifying the ultrasonic transducer contributing to the capturing of the pixel that has degraded performance.

20. A method for operating an ultrasonic sensing device comprising a plurality of ultrasonic transducers, the method comprising:
receiving an identification of defective ultrasonic transducers;
initiating an image capture operation by the plurality of ultrasonic transducers; and
during the image capture operation, adjusting the image capture operation to account for the defective ultrasonic transducers, wherein the adjusting the image capture operation to account for the identification of defective ultrasonic transducers comprises:
selecting ultrasonic transducers of the plurality of ultrasonic transducers that are not comprised within the identification of defective ultrasonic transducers to capture pixels of an image.

21. The method of claim 20, wherein the adjusting the image capture operation to account for the identification of defective ultrasonic transducers comprises:
selecting a beam forming pattern comprising a plurality of ultrasonic transducers that does not comprise ultrasonic transducers within the identification of defective ultrasonic transducers.

22. The method of claim 20, wherein the adjusting the image capture operation to account for the identification of defective ultrasonic transducers comprises:

adjusting a gain applied to at least one ultrasonic transducer of the plurality of ultrasonic transducers.

23. The method of claim 20, wherein the ultrasonic sensing device operation may be performed according to a plurality of modes providing different levels of performance and wherein the adjusting the image capture operation to account for the defective ultrasonic transducers is performed in at least one of the plurality of modes.

24. The method of claim 23, further comprising:
selecting the mode of the plurality of modes based at least in part on an application utilizing an image of the image capture operation.

25. A method for correcting an image captured at an ultrasonic sensing device comprising a plurality of ultrasonic sensors, the method comprising:
receiving an image captured at the ultrasonic sensing device;
receiving an identification of defective ultrasonic transducers of the ultrasonic sensing device; and
correcting pixels of the image to account for the identification of defective ultrasonic transducers.

26. The method of claim 25, wherein the correcting the pixels of the image to account for the identification of defective ultrasonic transducers comprises:
interpolating pixel values for adjacent pixels for pixels captured with at least one defective ultrasonic transducer.

27. The method of claim 26, further comprising:
subsequent the interpolating pixel values for adjacent pixels for pixels captured with at least one defective ultrasonic transducer, providing the image comprising interpolated pixel values to an image matcher.

28. The method of claim 26, further comprising:
providing information related to the pixels of the image that were corrected to an image matcher.

29. The method of claim 25, wherein the correcting the pixels of the image to account for the identification of defective ultrasonic transducers comprises:
adjusting a gain calibration for at least one pixel according to a contribution of at least one defective ultrasonic transducer to the image.

30. A method for detection of defective ultrasonic transducers in an ultrasonic sensing device, the method comprising:
detecting a self-test condition, wherein the self-test condition comprises at least one of a thermal shock event or a mechanical shock event;
generating an ultrasonic signal at an ultrasonic sensing device comprising a plurality of ultrasonic transducers, wherein the generating the ultrasonic signal is initiated responsive to detecting the self-test condition;
receiving a reflected ultrasonic signal corresponding to the ultrasonic signal at at least one ultrasonic transducer of the plurality of ultrasonic transducers; and
determining whether performance of the at least one ultrasonic transducer is degraded based at least in part on the reflected ultrasonic signal.

31. A method for detection of defective ultrasonic transducers in an ultrasonic sensing device, the method comprising:
generating an ultrasonic signal at an ultrasonic sensing device comprising a plurality of ultrasonic transducers;
receiving a reflected ultrasonic signal corresponding to the ultrasonic signal at at least one ultrasonic transducer of the plurality of ultrasonic transducers;
determining whether performance of the at least one ultrasonic transducer is degraded based at least in part on the reflected ultrasonic signal;
maintaining an inventory of ultrasonic transducers having degraded performance; and
during image capture, selecting ultrasonic transducers of the plurality of ultrasonic transducers that are not determined as having degraded performance.

* * * * *